United States Patent [19]

Dorne

[11] Patent Number: 5,325,293
[45] Date of Patent: Jun. 28, 1994

[54] SYSTEM AND METHOD FOR CORRELATING MEDICAL PROCEDURES AND MEDICAL BILLING CODES

[76] Inventor: Howard L. Dorne, 7 Blue Ridge, Irvine, Calif. 92720

[21] Appl. No.: 838,493

[22] Filed: Feb. 18, 1992

[51] Int. Cl.$^5$ ............................................. G06F 15/21
[52] U.S. Cl. ............................... 364/413.01; 364/401
[58] Field of Search ........... 364/401, 406, 408, 413.01, 364/468, 478, 403

[56] References Cited

U.S. PATENT DOCUMENTS

| | | | |
|---|---|---|---|
| 4,491,725 | 1/1985 | Pritchard | 364/413.01 |
| 4,667,292 | 5/1987 | Mohlenbrock et al. | 364/413.01 |
| 5,001,630 | 3/1991 | Wiltfong | 364/413.01 |

OTHER PUBLICATIONS

Cerner ® Corporation Brochure, "RadNet TM Radiology Information System" (1989).
Sunquest Information Systems, Inc. Brochure, "FLEXiRAD TM Overview" (1990).
Digital Brochure, "VAX DECrad" (1990).
Digital, "VAX DECrad V4.0 Guidebook" (1990).
American Medical Association, *1992 Physicians' Current Procedural Terminology* (4th Edition 1991).
SD&E Healthcare Systems, Inc. Brochure, "IMAGES/3000 Radiology Management System" (1991).
American College of Radiology, "New Physician Payment Rules 1992 Medicare Fee Schedule" (1991).
HBO & Company Brochure, "CLINSTAR-Radiology" (1991).
DuPont Brochure, "The DuPont Micro Radiology Manager TM System: Information Management That Fits Your Needs".
Sunquest FLEXiRAD TM Brochure, "Introducing FLEXiRAD TM ".
HBO & Company, "Release 11.1 Overview, Focusing on the Vision".
HBO & Company, "CLINSTAR-Radiology".

*Primary Examiner*—Roy N. Envall, Jr.
*Assistant Examiner*—Jennifer L. Hazard
*Attorney, Agent, or Firm*—Knobbe, Martens, Olson & Bear

[57] ABSTRACT

A method and a system for performing the inventive method are provided to correlate billing codes with planned or performed medical procedures. The method comprises the steps of determining raw codes directly associated with all of the medical procedures performed or planned to be performed with a particular patient examination, and manipulating the raw codes by the steps of a final common pathway to generate intermediate codes without altering the raw codes. The method also comprises the step of determining the billing codes from the intermediate codes.

23 Claims, 42 Drawing Sheets

CATHMAN

Patient Demographics

Medical Records Number: 0000010     Birthdate: 1/1/60

Last Name: JONES

First Name: JOHN     Middle Initial: J

Sex: M     Social Security Number: 000 - 00 - 0000

Street Address: 123 MAIN STREET

City: IRVINE

State [CA]: CA     ZIP: 92627 - 1234

Home Phone: 714 - 555 - 1212

Work Phone: 714 - 555 - 1234

Comments:

Accept Data — 120

Cancel

| Procedural Categories | Anatomic Locations | Procedures | Additional Parameters |
|---|---|---|---|
| Arteriography | Aortic, abdominal<br>Aortic, thoracic<br>Bronchial<br>Carotid<br>Extremity, lower<br>Extremity, upper<br>Mesenteric<br>Pelvic<br>Pelvic, selective<br>Pulmonary<br>Spinal<br>Subclavian<br>Vertebral | Celiac<br>SMA<br>IMA<br>Supraselective Celiac<br>Supraselective SMA<br>Supraselective IMA<br>Aortogram | Select No. of separate second order supraselective studies beyond the Celiac artery |
| Cardiac | | | |
| Interventional | | | |
| Miscellaneous | | | |
| Patient Care | | | |
| Venography | | | |

FIG. 4

SYSTEM AND METHOD FOR CORRELATING MEDICAL PROCEDURES AND MEDICAL BILLING CODES

BACKGROUND OF THE INVENTION

1. Field of the Invention

The present invention relates to a system and a method for correlating medical procedures and medical billing codes and, in particulate, to a system and a method for correlating interventional radiology procedures to medical billing codes.

2. Description of Related Art

The Health Care Financing Administration (HCFA-)—the government agency assigned the responsibility of overseeing the Medicare program—had adopted the Physician's Current Procedural Terminology (CPT) medical coding system of the American Medical Association (AMA) for reporting physicians' services to the Medicare program and to calculate the fees and costs associated with such services. The Medicare payment system, starting in 1992, is based upon a resource based relative value scale which assigns specific relative value units (RVU) to each specific procedure corresponding to a CPT code, The majority of private insurance companies have also started using the CPT coding system as a basis for their payment schedules. Accordingly, physicians must code their examination procedures according to the CPT coding system in order to be paid for their services from these organizations, The AMA has structured the CPT coding system into five main procedure rubrics: Medicine; Anesthesia; Surgery; Radiology; and Pathology. The CPT coding system uses a five digit code to identify a particular type of procedure within each rubric, Each code typically covers a category of specific medical procedures. For example, a vascular injection into the right common carotid falls under the Surgery codes and, in particular under the procedural category of introducing a needle or intracatheter into an initial second order vessel within a vascular family of the thoracic or the bracheocephalic branches (specifically CPT code 36217).

Some medical specialists find the CPT coding system difficult to use because many modern medical specialties fall within several of the enumerated rubrics. For instance, Interventional Radiologists ("Interventionalists") especially view the new coding system as arduous because interventional radiology crosses many radiological and surgical sub-specialties, each of which falls under a specific CPT coding system rubric. For instance, if a radiologist examines a patient's left vertebral artery, the corresponding CPT codes for the examination would contain both Surgical codes and Radiology codes. Specifically, the CPT codes for this examination would be 36216 for the surgical component of the examination and 75685 for the radiological component of the examination.

Another complication of the CPT coding system specific to interventional radiologists is that the surgical codes for angiographic procedures require the interventionalist to identify the number of vascular families catheterized as well as the "order" of the vessel that was studied.

A vessel family is a group of vessels that share a common vessel or origin arising from either the aorta or one of the vena cavae. For example, the right renal artery and all of its branches represent one vascular family, the common origin of which is the main right renal artery. The order of a vessel is defined as follows: a first order vessel is the first branch or tributary of a family that arises from the aorta or one of the vena cavae; a second order vessel is simply the next branch or tributary of a first order vessel; and a third order vessel is the next branch or tributary of a second order vessel.

Within each vascular family, the properly assigned CPT code corresponds to the highest order of vessel catheterized. Additional third order and second order vessels studied within a vascular family also receive credit. The first order and higher order fees already include the fee for non-selective catheterization (i.e., catheterization of the aorta or one of the vena cavae), and, thus, the non-selective catheterization is not charged separately.

The CPT coding system requires a working knowledge of the medical procedures involved in order to receive proper compensation, and, thus, clerical personnel commonly improperly code examinations. Because an accountant or billing clerk typically does not understand the medical procedures involved, many performed procedures not identified by the physician in the CPT coding format go unbilled. Furthermore, even if the person coding the examinations understands the procedures involved, he or she is likely to overlook some intermediate procedures. Moreover, correlating the CPT codes with the procedure involved is virtually impossible without fully understanding the medical nomenclature used by the CPT coding system.

Additionally, physicians and clerical personnel often do not accurately translate the performed medical procedure into the CPT coding format because of the complexity of the CPT coding system. For example, if a radiologist examines a right vertebral artery by arteriography, including a vascular injection, one particular CPT code would correspond to the vascular injection. However, if the radiologist additionally examines a patient's right common carotid, a different CPT code would correspond to the vascular injection associated with the examination of the patient's right vertebral. In many situations, a straight reading of the CPT code will not provide the proper billing code and the physician or clerical personnel must review an entire CPT rubric to determine the proper billing code, or must memorize how certain procedural codes interact. Memorizing all of CPT codes applicable to the physicians' practice, however, would be impracticable (in the case of the interventionalist, it would be impossible), and using a truncated, but manageable list would be inaccurate. Thus the physician is forced to learn the workings of each applicable CPT rubric, a tedious and time consuming task, exacerbated by the fact that the CPT codes commonly change from year to year.

The CPT coding system is also imprecise in some areas and the physician and/or clerical personnel must learn to compensate for the inexactness of the CPT coding system. For instance, if a radiologist examines a patient's celiac and superior mesenteric arteries, the CPT coding system does not provide separate codes for these vascular families. Moreover, the CPT coding system does not provide separate codes for examination of particular vessels within these vascular families. The physician and/or clerical personnel must therefore realize that a duplicate CPT code for this procedure would be appropriate and code the examination accordingly.

Because of the complexity of the CPT coding system outlined above, payments from Medicare and private insurance companies commonly lack parity with the physician's services. Moreover, physicians are commonly required to code examinations themselves because the CPT coding system demands a thorough understanding of the medical nomenclature used by the CPT code. However, coding is a time consuming task for a busy physician.

Thus, a need exists for a method and a system for implementing the method for rapidly and simply correlating CPT codes with medical procedures performed during a patient examination which does not require a thorough understanding of the nomenclature used by the CPT coding system.

SUMMARY OF THE INVENTION

The present invention comprises a system and a method for correlating medical procedures into billing codes. The system performing the inventive method translates medical procedures into accurate billing codes, such as, for example CPT codes. The system additionally allows a physician to plan medical procedures in advance, allows the physician to modify the planned procedures after performing the examination, and then automatically translates the performed procedures into billing codes to maximize the procedures billed.

One embodiment of the present invention comprises a method of generating official billing codes in response to selected medical procedures. The method comprises the steps of generating raw codes associated with the selected medical procedures and analyzing the raw codes to generate a set of intermediate codes which account for the interrelation of the selected medical procedures without altering the raw codes. The method additionally includes the step of generating a set of billing codes from said intermediate codes.

In a preferred embodiment of the present invention, an interactive computer program advantageously embodies the inventive method. The interactive program desirably runs on a standard AT compatible 80386 or 80486 computer platform, or the like, and operates in a "MICROSOFT" "WINDOWS" graphic environment. The interactive program preferably stores dedicated examination screen data in each examination record such that when a user recalls an examination record, the interactive program recalls the specific examination screen associated with the preselected procedures.

BRIEF DESCRIPTION OF THE DRAWINGS

These and other features of the invention will now be described with reference to drawings of a preferred embodiment which is intended to illustrate and not to limit the invention, and in which:

FIGS. 2A through 2J are representations of several illustrative initial screen displays generated by an interactive program embodying the present invention;

FIG. 4 is a branching diagram used with the present invention illustrating a preferred order of screen displays generated by the interactive program embodying the present invention;

DETAILED DESCRIPTION OF THE INVENTION

Figure 1:
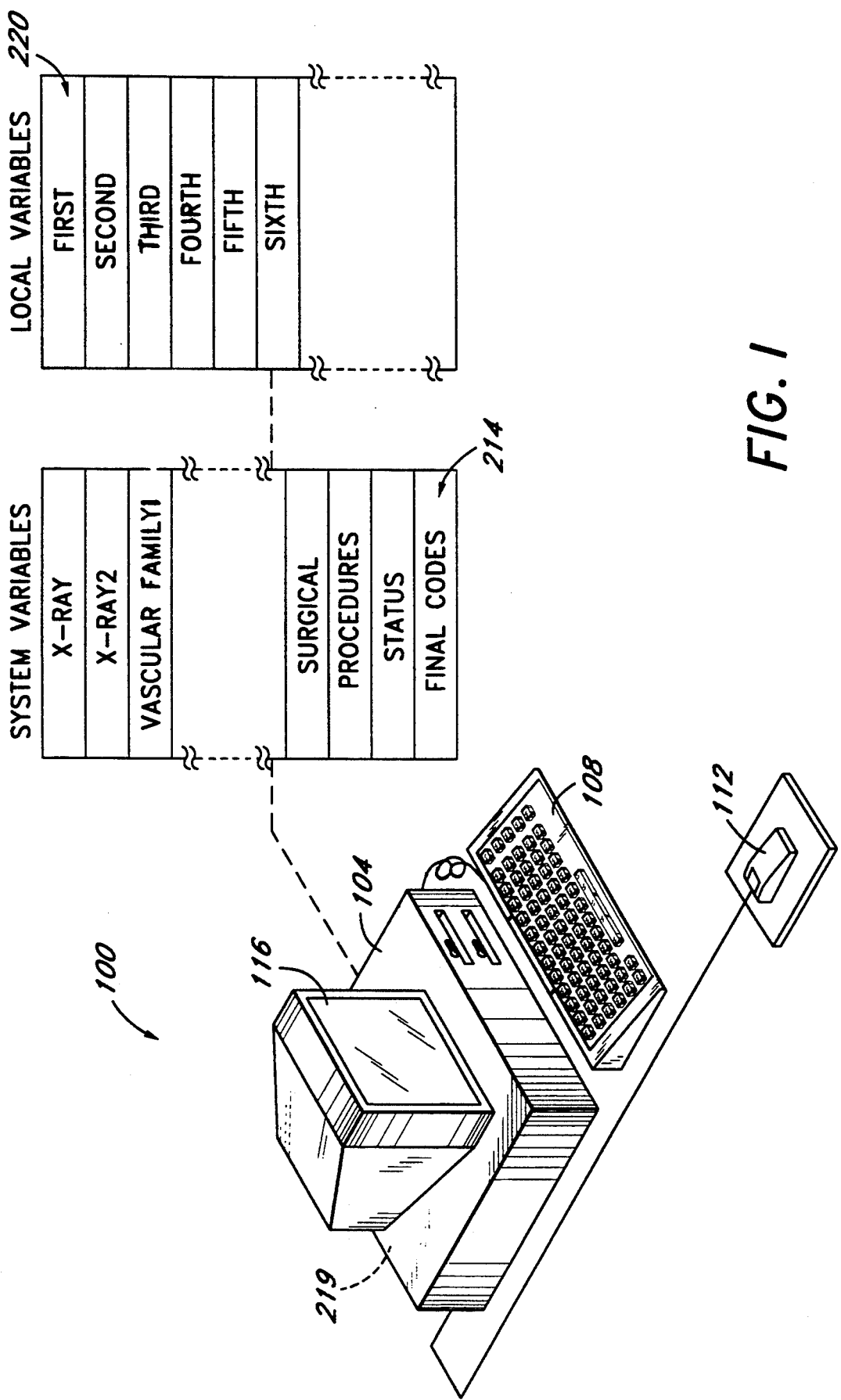
FIG. 1 schematically illustrates a computer system in which with the present invention is intended to be used.

The present invention is intended to be used with a computer system 100 of the type illustrated in FIG. 1. The computer system 100 includes a standard computer platform 104, which preferably is an AT compatible computer that includes an Intel 80386 or 80486 CPU, or the like, with supporting extended industry standard architecture. A user typically communicates with the computer platform 104 through an interface 108, such as, for example, a keyboard, and/or through a data selector 112, such as for example, a mouse, roller-ball or the like. A video display monitor 116 displays interactive screens which commonly include a movable cursor or like marker which the user controls via the keyboard 108 and/or the mouse 112. The user typically interacts with the computer platform 104 by positioning the cursor on a screen view item and entering a selection by actuating a bipolar switch, such as an Enter or Return key or alphanumeric key on the keyboard 108, or the mouse button. The user can also enter numeric or alphanumeric data into input fields of a screen through the keyboard 108.

An interactive computer program adapted for use with the computer platform 104 described above embodies a preferred embodiment of the present invention. The interactive computer program preferably operates in the Microsoft ® Windows ™ graphical environment and is written in a source code compatible with "MICROSOFT" "WINDOWS", such as, for example, "TOOLBLOCK" by Asymetric Corporation.

The interactive computer program embodying the present invention generates CPT codes "automatically," without requiring the users to enter the codes themselves. The user does not need any detailed knowledge of CPT coding techniques to code examination procedures quickly and accurately.

FIGS. 2A through 3G and 5A through 8B illustrate a series of screen displays generated by the interactive program at different stages of a method for correlating CPT codes with performed examination procedures in accordance with one embodiment of the present invention. The particular order of the screen displays illustrated in these figures is understood to illustrate the use and operation of the invention and is not to be in any way limiting on the scope of the present invention. In addition, the illustrated preferred embodiment of the present invention relates to the practice of interventional radiology; however, it is understood that those skilled in the art could apply the present invention in other medical fields.

Figure 2A:
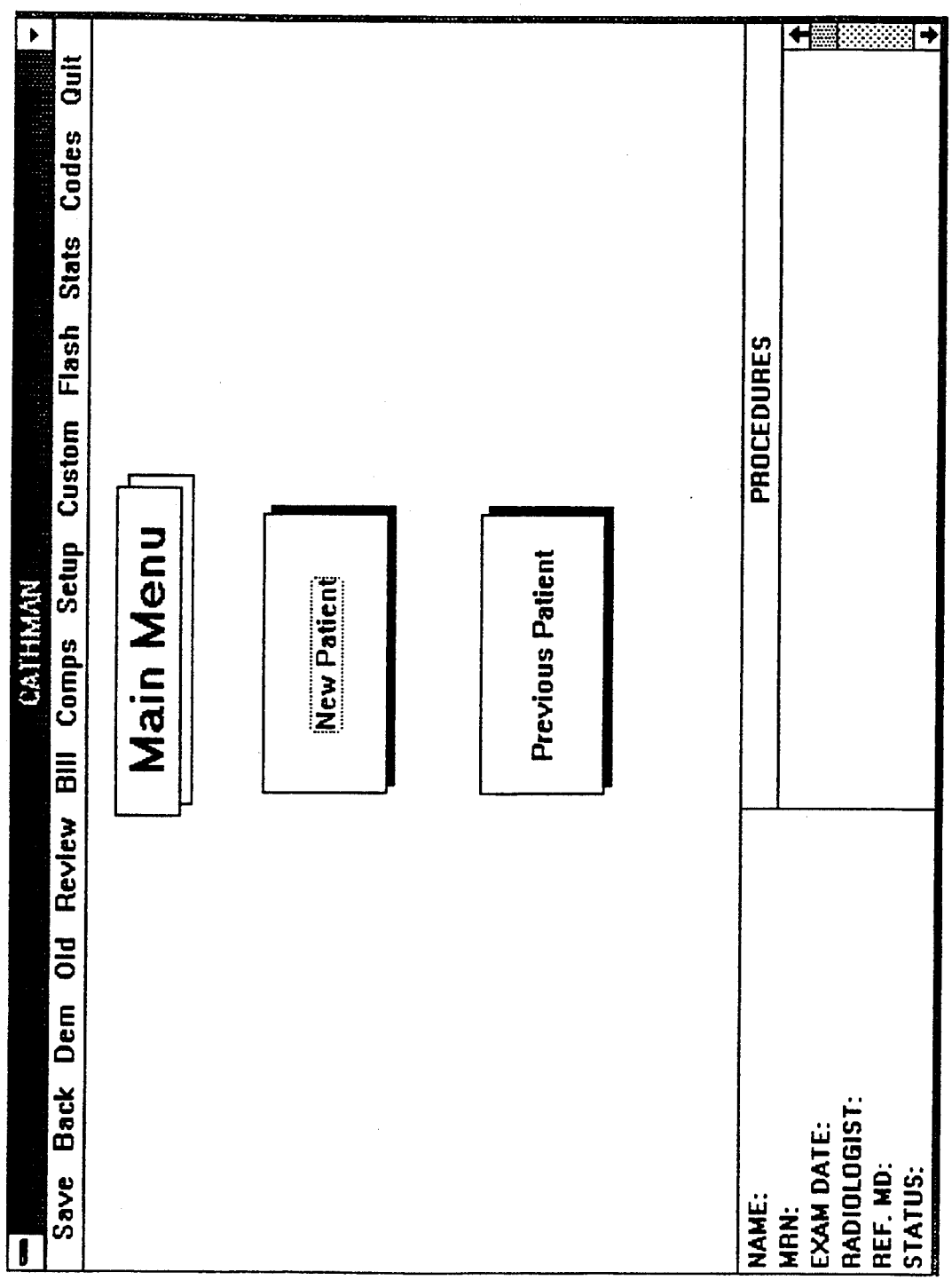

At an initial screen, as illustrated in FIG. 2A, the interactive program gives the user a choice of entering an examination for a new patient or recalling an examination for a previous patient. If the user chooses a new patient, the interactive program requests the user to enter the new patient's demographics, as illustrated in FIG. 2B. Although the user does not have to enter data into every field on the demographics screen, the patient's medical record number and name should be entered before exiting the screen. After entering the data in the appropriate fields, the user inputs the data by clicking the mouse button with the cursor on the "accept" button 120.

Figure 2C:
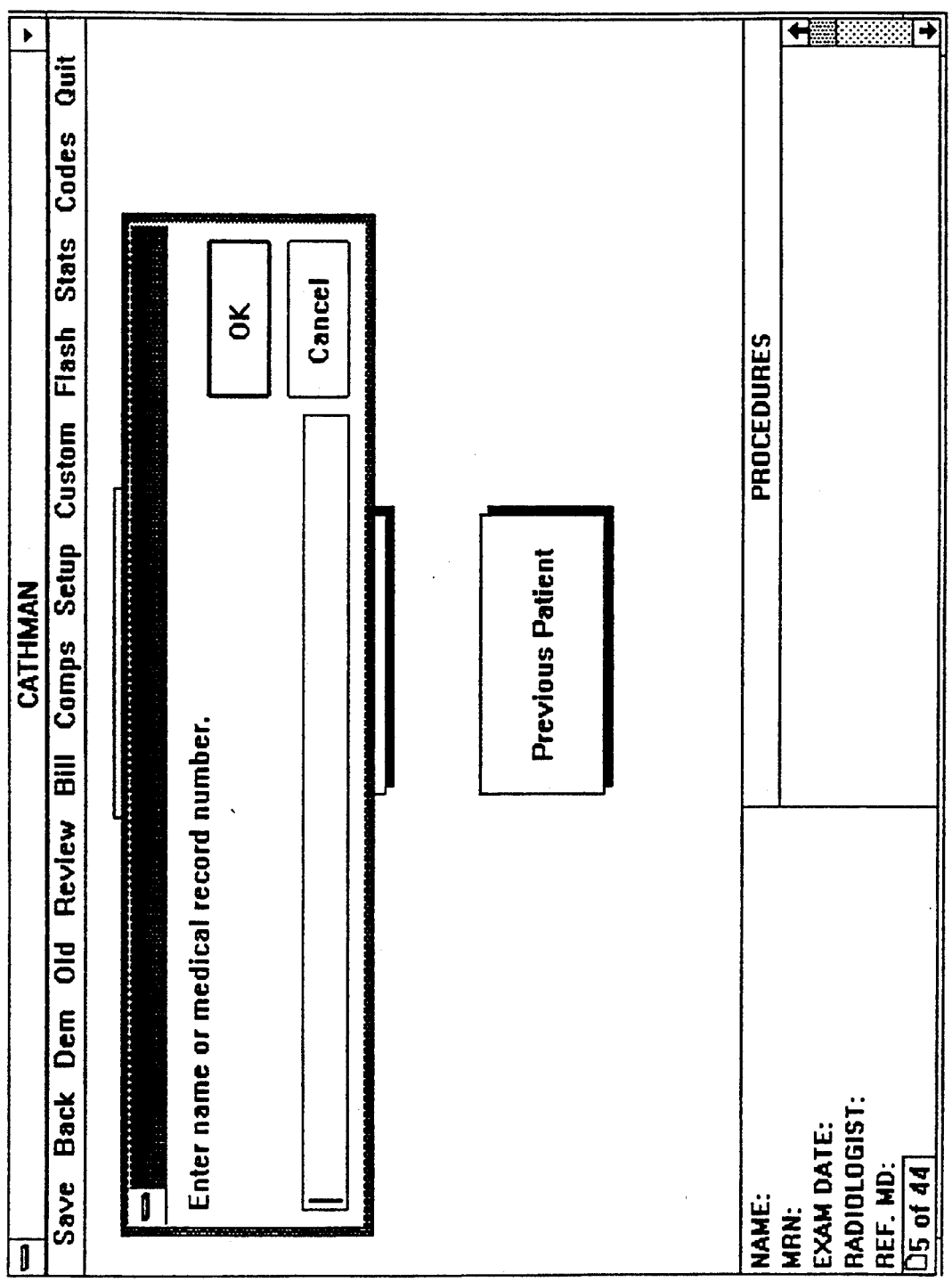
Figure 2D:
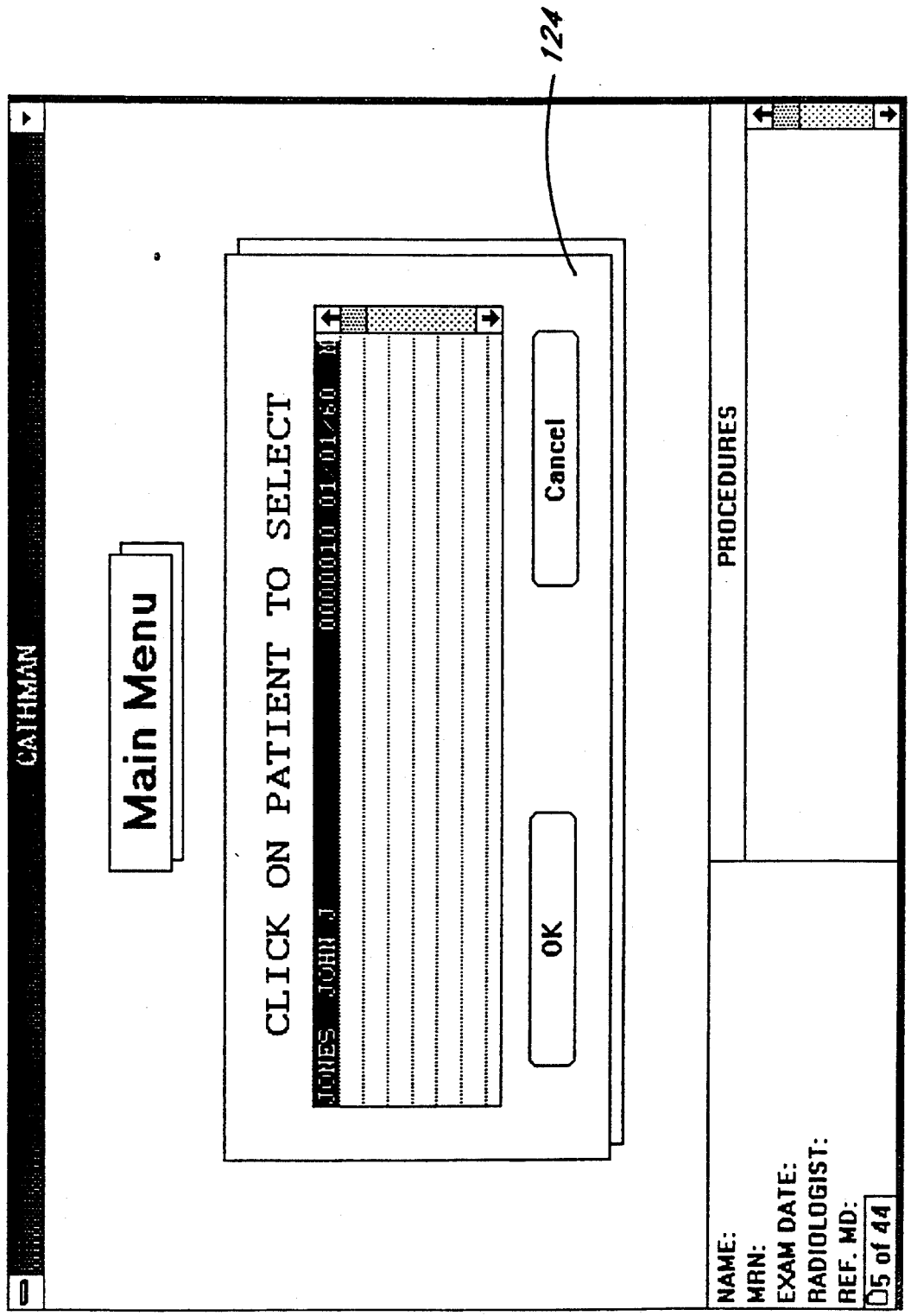

If the user chooses a previous patient, the user enters either the name or identification number of the previous patient, as requested by the interactive screen illustrated in FIG. 2C. The interactive program then recalls the demographics for the previous patient. The user of the interactive program can set a desired field length of the identification number to customize the program. If the user enters the last name of the patient, the interactive program will display all patients with that last name in a scroll-type menu 124 as illustrated in FIG. 2D.

Figure 2E:
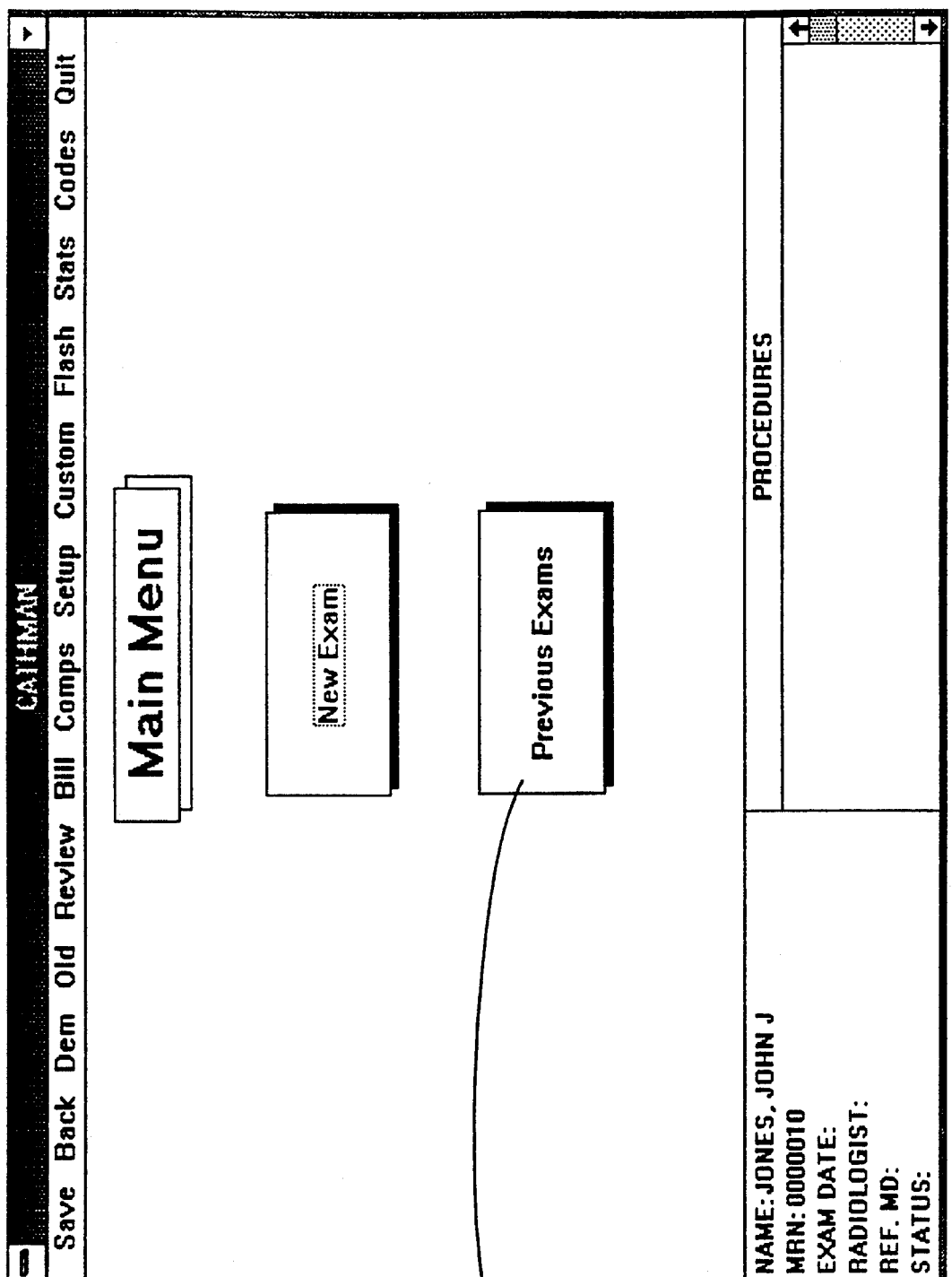
Figure 2F:
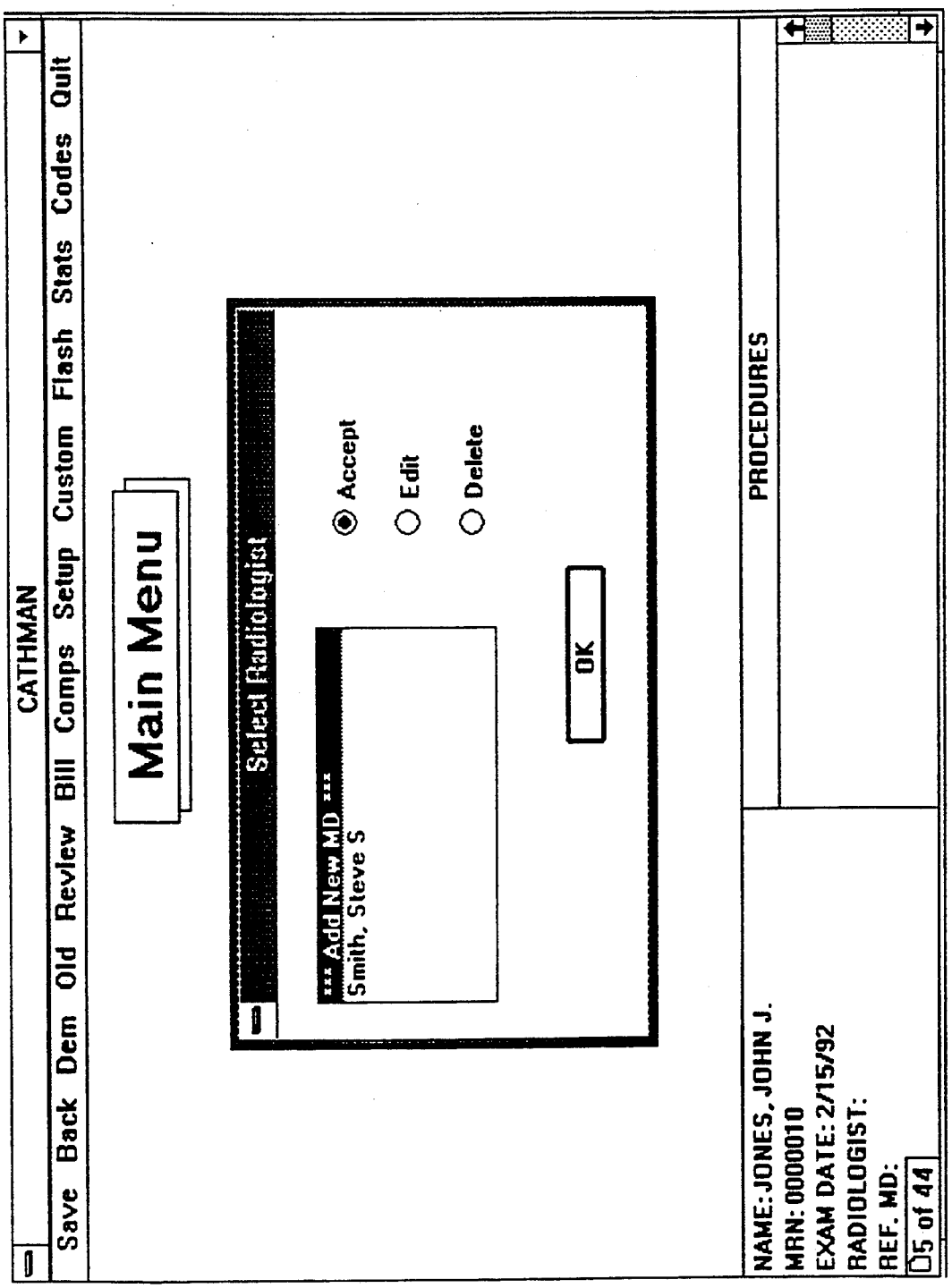
Figure 2G:
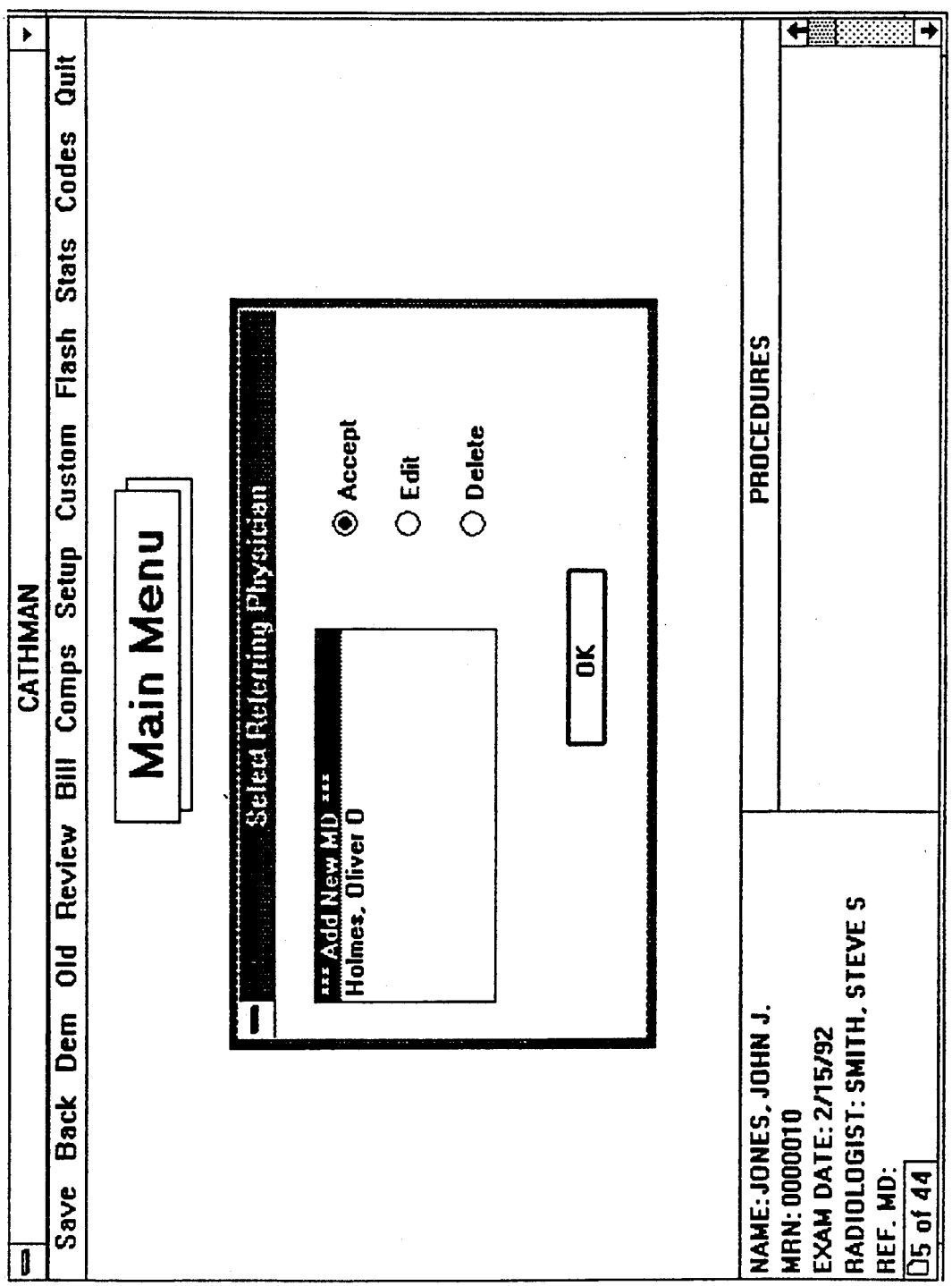
Figure 2H:
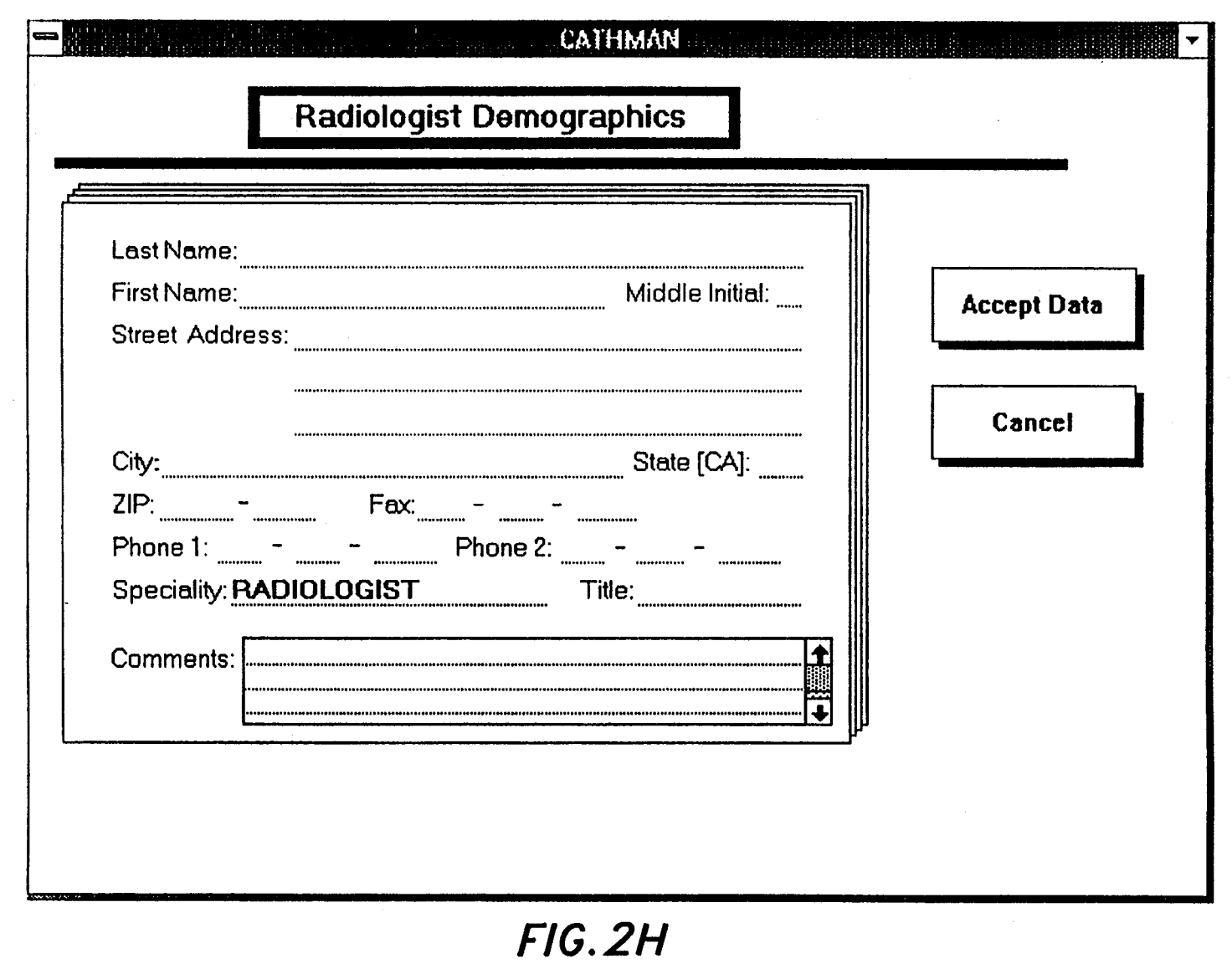

Referring to FIG. 2E, the interactive program requests the user to select a new examination or recall a previous examination after choosing a patient. For a new examination, the interactive program displays a series of dialogue boxes to request data about the examination. The user is asked to enter the date of the examination and the name of the radiologist and of the referring physician. Specifically, after entering the name of the radiologist or referring physician, the interactive program will display a list of radiologists or referring physicians contained in memory, as illustrated by FIGS. 2F and 2G, respectively. If the particular doctor is presently in the memory file, the user highlights the name of the doctor and accepts the data. If, however, the radiologist or referring physician is not contained in the memory file of the interactive program, the interactive program requests the user to input the demographics for the radiologist and/or referring physician, as illustrated in FIGS. 2H and 2I. Alternatively, if the interactive program recognizes the names of the radiologist and referring physician, the interactive program will request the user to verify the selection.

Figure 2J:
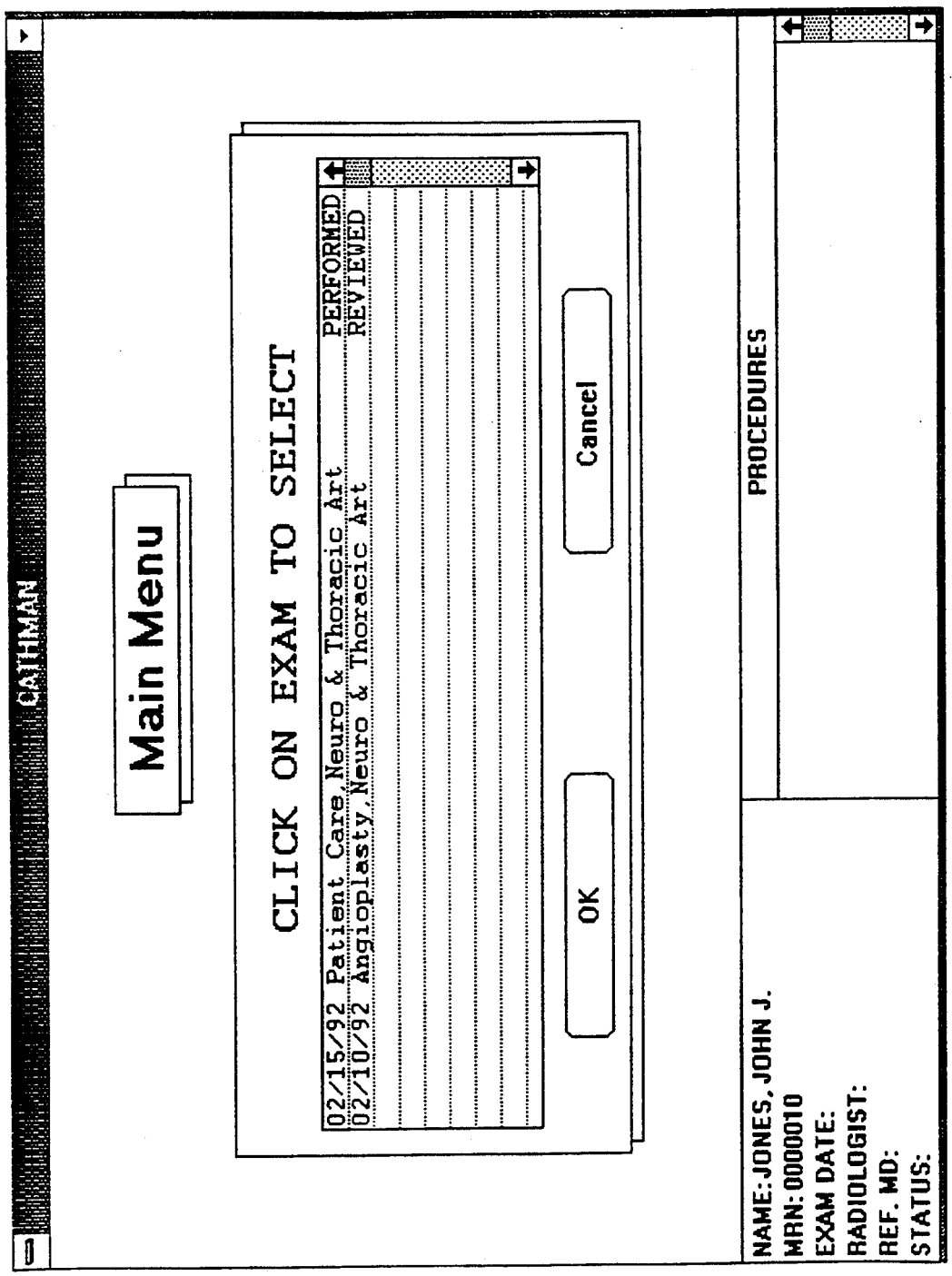

To recall a previous examination, the user selects the PREVIOUS EXAMS button 128 (FIG. 2E) via the mouse controlled cursor. The interactive program will then display a list of previous examinations for the previously selected patient, as illustrated in FIG. 2J.

Figure 3A:
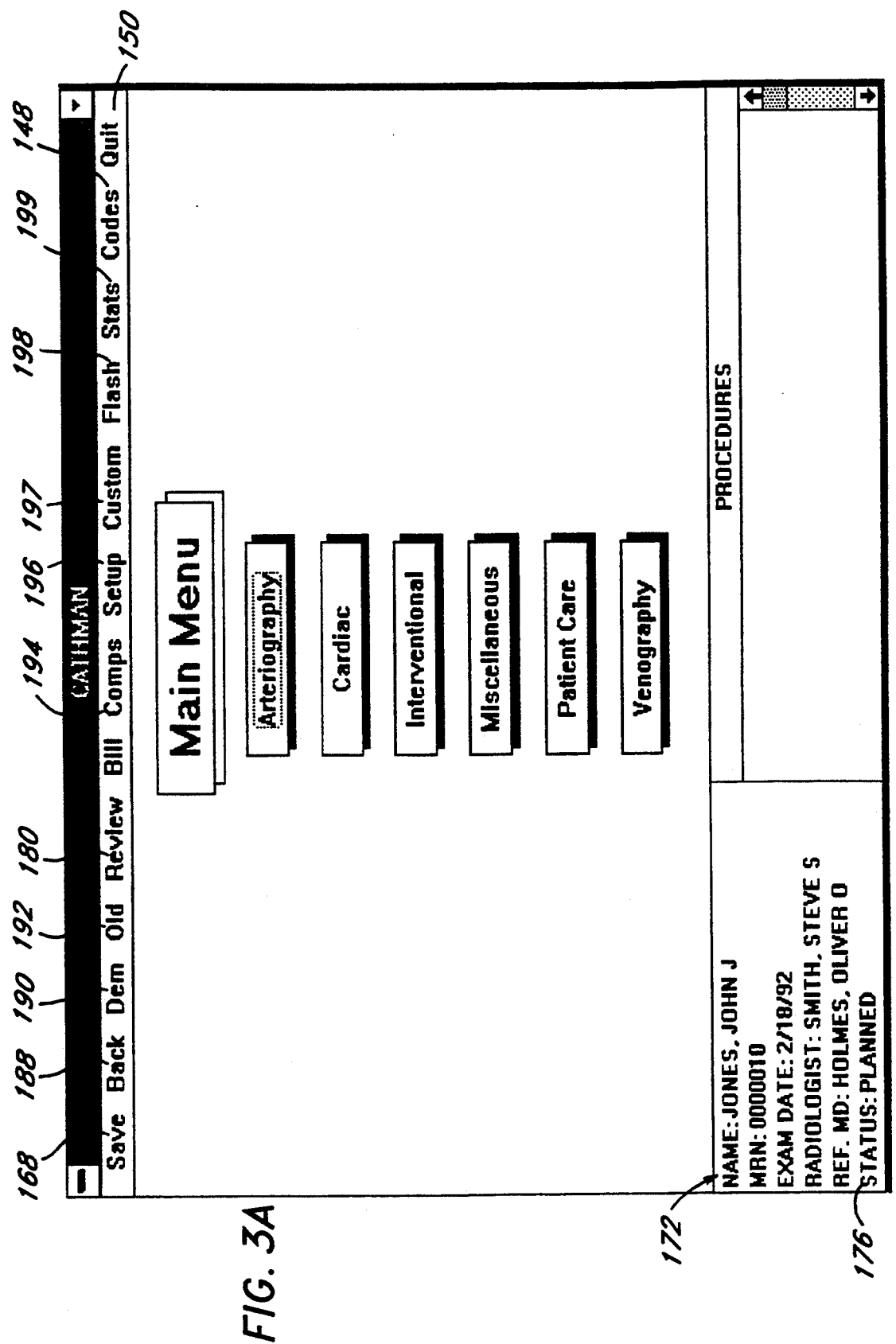
FIGS. 3A through 3G are representations of several illustrative screen displays generated by the interactive program showing the branching of procedural menus.
Figure 3B:
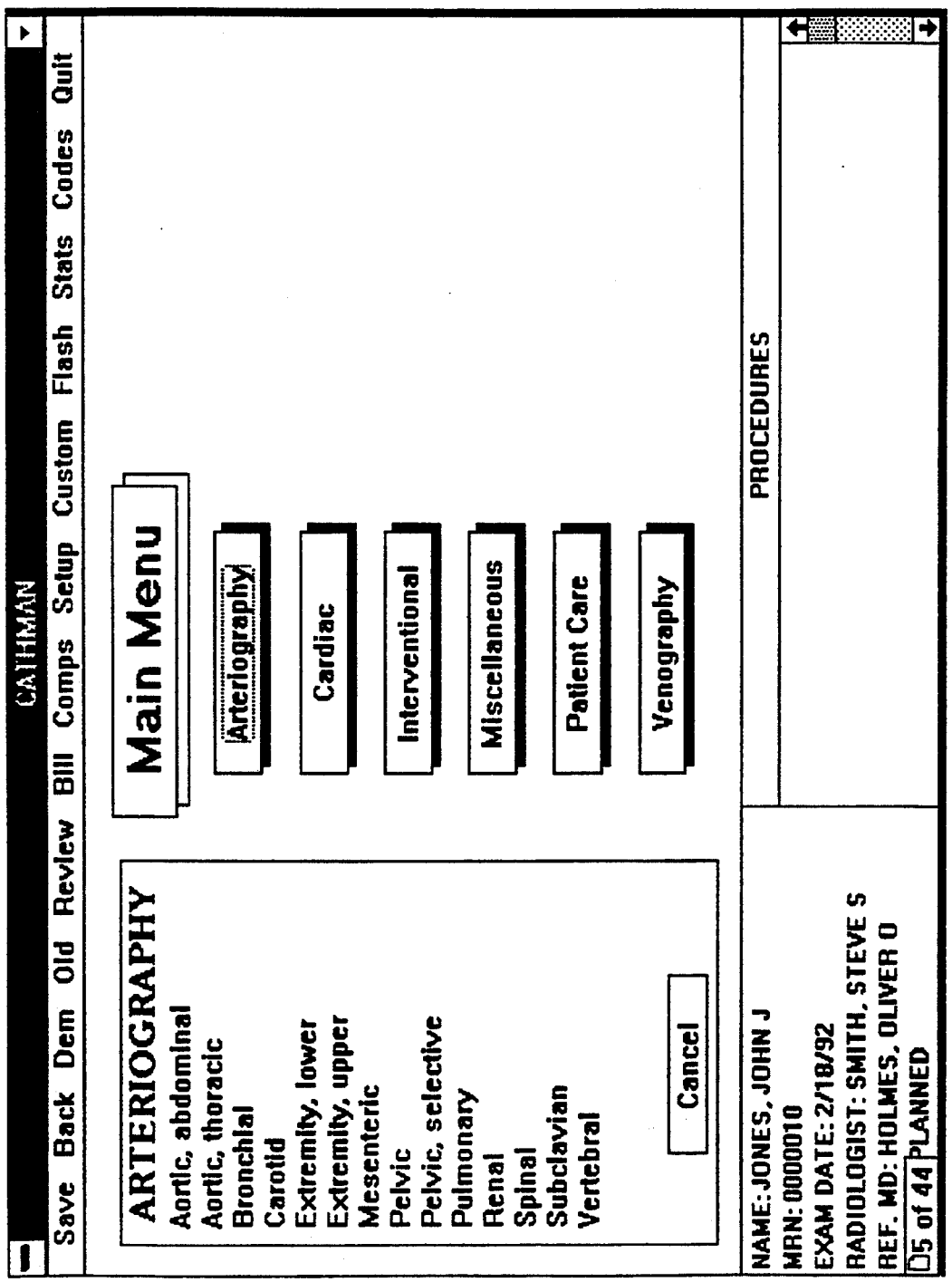

After the user has selected a patient and has either entered the preliminary data for a new examination or recalled the data from a previous examination, the interactive program displays a Main Menu screen, as seen in FIG. 3A, which includes six procedural group buttons corresponding to major categories of interventional work. These categories are: Arteriography, Cardiac, Interventional, Miscellaneous, Patient Care and Venography. As illustrated in FIG. 3B, if the user moves the cursor over any of the procedural group buttons, the interactive program flashes a related procedure menu on the left side of the screen.

The procedure menus list major types of procedures contained in each interventional category. Each listing is a "hotword." A hotword is defined as a word that causes an action to happen when actuated by the mouse controlled cursor (i.e., is clicked upon). Clicking on a procedure hotword exits the Main Menu screen and displays an examination screen associated with that procedure. To remove a procedure menu without selecting one of its choices, the user clicks the CANCEL button 132 found at the bottom of the procedure menu.

The procedure menus list a variety of procedures contained in each major category. For example, by selecting the Aortic, thoracic, the interactive program displays an examination screen (FIG. 3C) containing a variety of related procedures. The examination screen contains multiple buttons, each of which represents a procedure. Several examination screens have one or more sub-screens to handle the large number of procedures grouped under one type of examination. For instance, the examination screen illustrated in FIG. 3C contains an ADDITIONAL SELECTIVES button 136. By clicking on the ADDITIONAL SELECTIVES button 136, the interactive program displays a second screen (not shown) containing the additional procedural buttons grouped under "Thoracic, Cervical and Cranial Arteriography" procedural category. The interactive program may also display additional level screens containing the balance of the procedural buttons grouped under a common examination screen title.

All examination screens have the same basic format. Each screen contains at the top of the screen a title describing the type of examination found on the screen. The screen also typically contains on the left side a procedure drawing. The procedures drawing symbolizes the procedure contained on the examination screen, as discussed in detail below. In addition to the procedure buttons, the examination screens include a procedures field which describes textually which procedure buttons the user has activated.

The user interacts with the interactive program by selecting specific procedure buttons corresponding to a planned examination or a performed examination. The interactive program confirms the user's selection by highlighting a segment of the procedure drawing to symbolize which vessels were involved in the procedure. For instance, FIG. 3D illustrates an examination involving the three procedures described by the procedures field with the vessels involved in the selected procedures are highlighted in the procedure drawing. In a preferred embodiment, the interactive program changes the colors of the buttons corresponding to the selected procedures on the examination screen and colors the highlighted vessels.

The bottom right corner of most examination screens contains two buttons labelled MAIN MENU and ASSOCIATED EXAMS. The user clicks on the MAIN MENU button 140 to return to the Main Menu screen. Clicking or passing over the ASSOCIATED EXAM button 144 with the cursor brings up an Associated Examination menu. The Associated Examinations menu lists examinations that are often performed at the same time as the examination procedures on the current screen. This provides the advantage of reminding the user to determine whether any such associated examinations were also performed. FIG. 3E illustrates the Associated Examination menu displayed if the user clicks on the ASSOCIATED EXAMS button 144 of the examination screen illustrated in FIG. 3D.

Figure 3C:
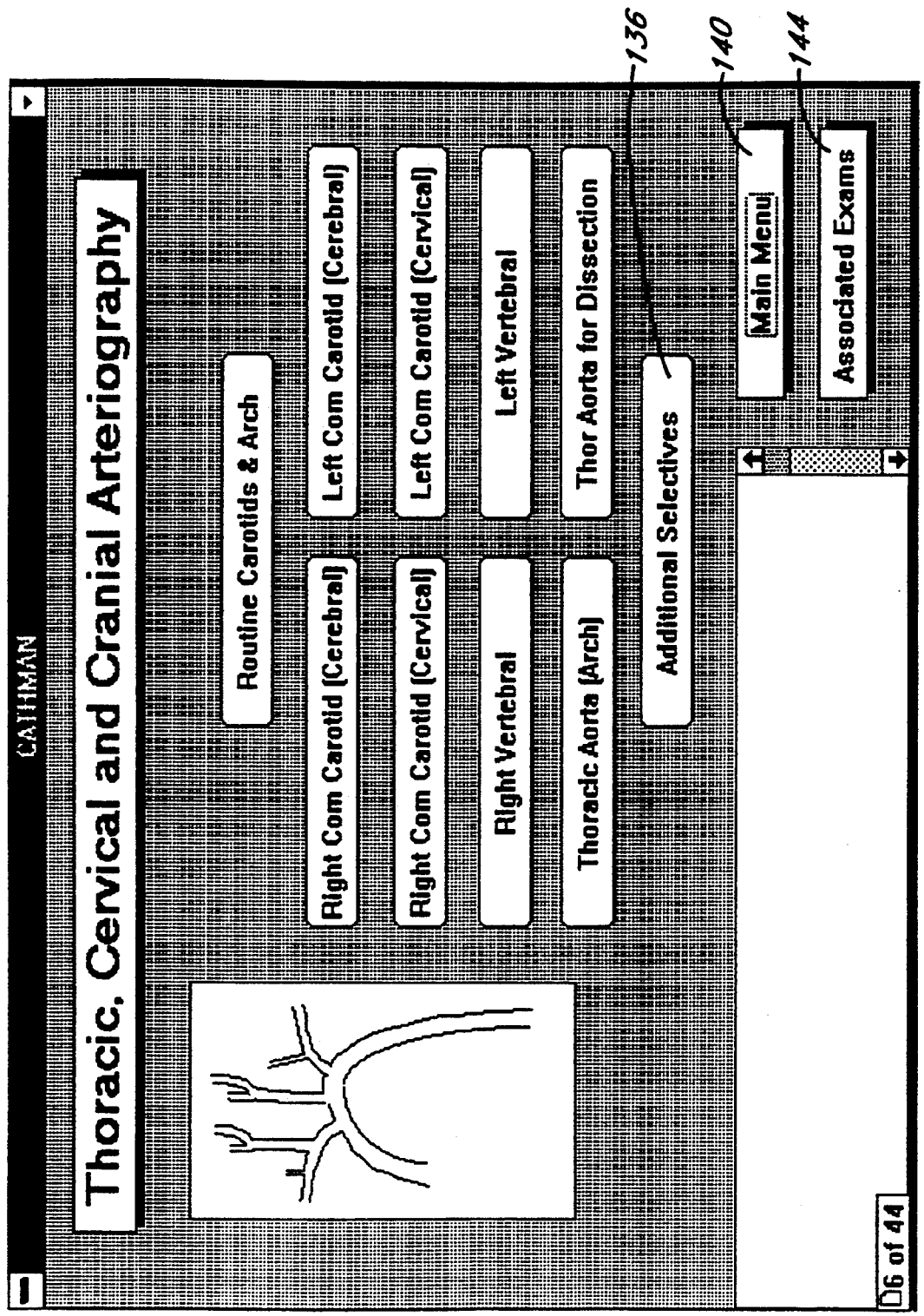
Figure 3D:
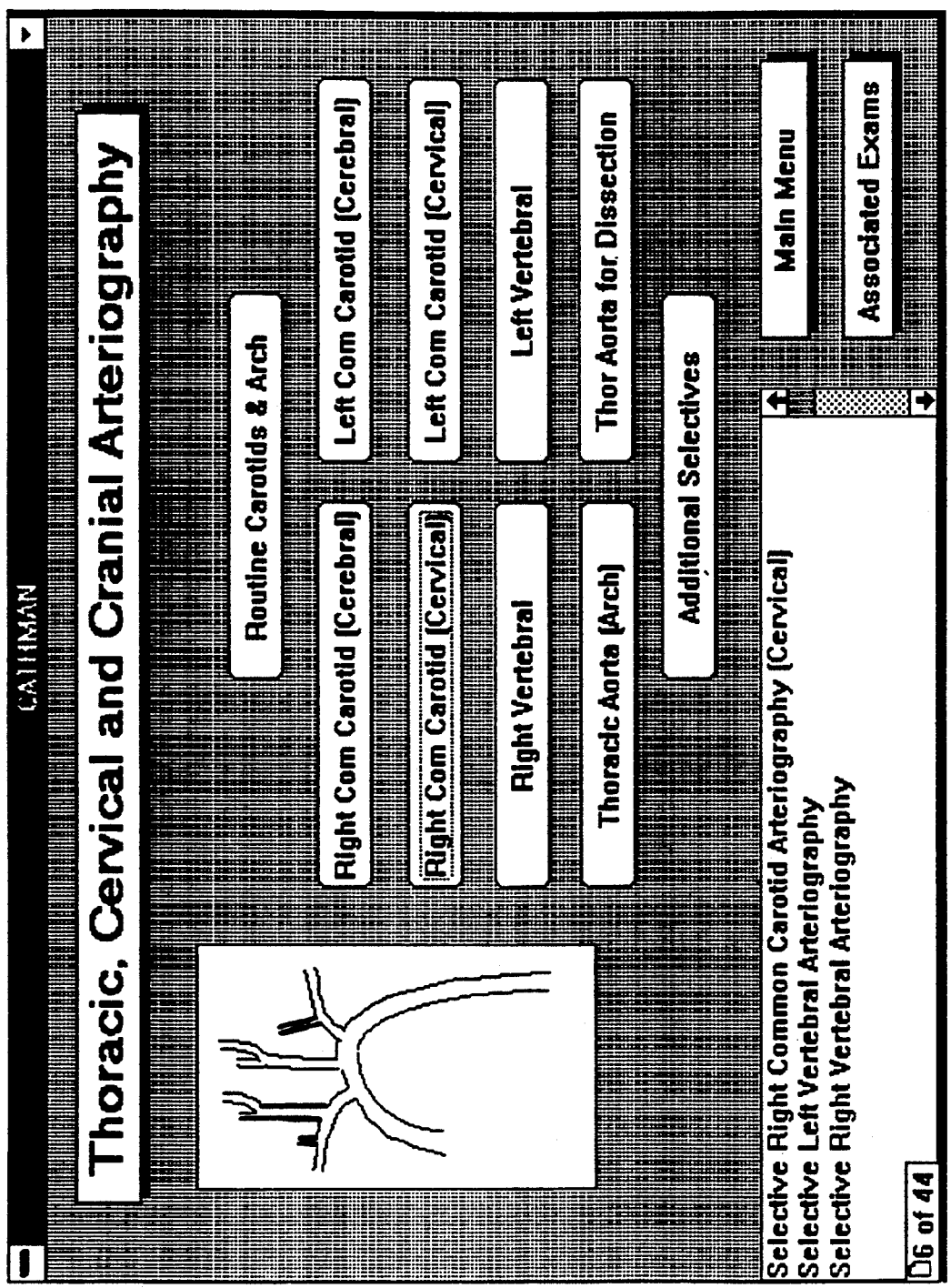
Figure 3E:
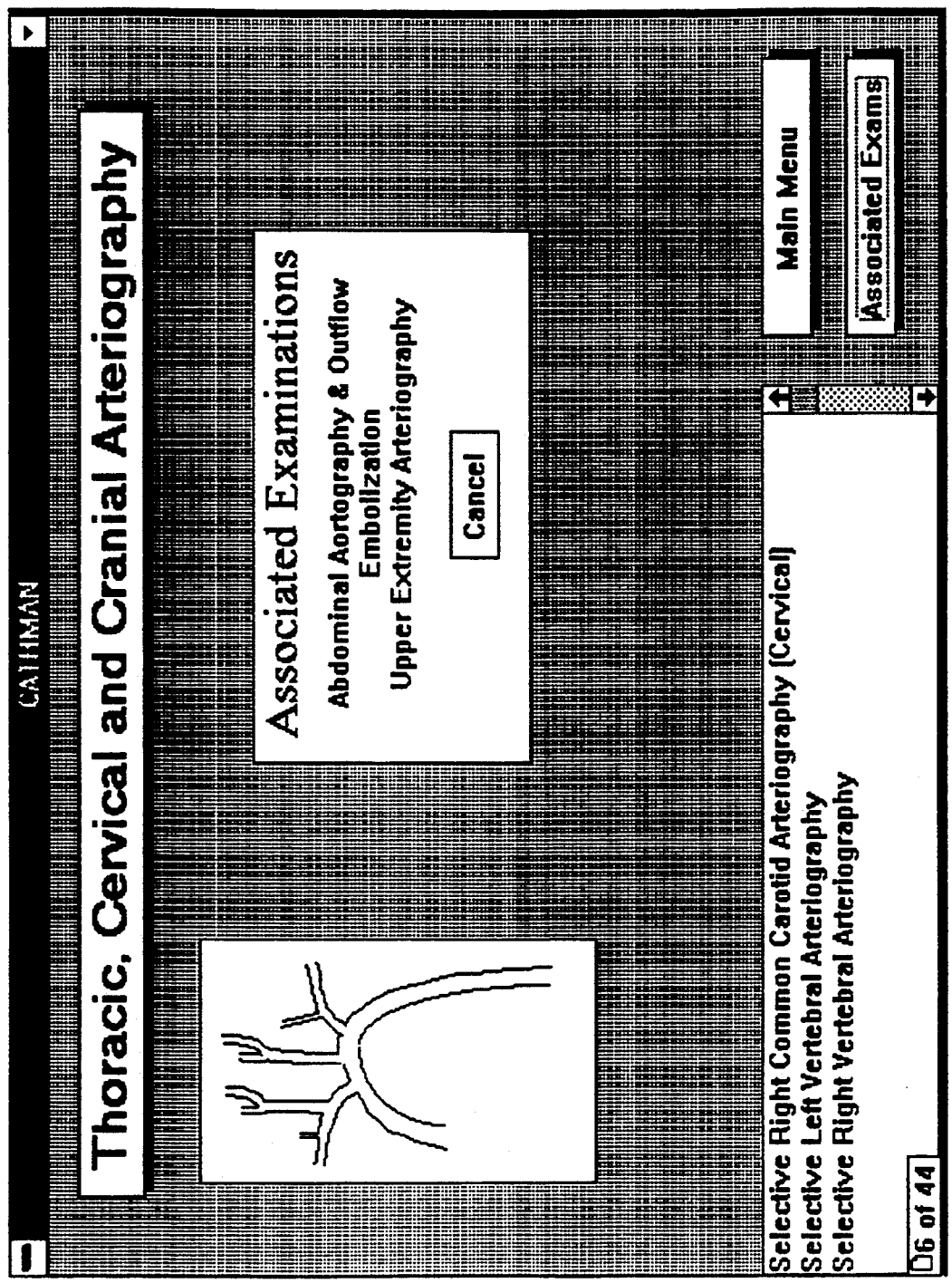
Figure 3F:
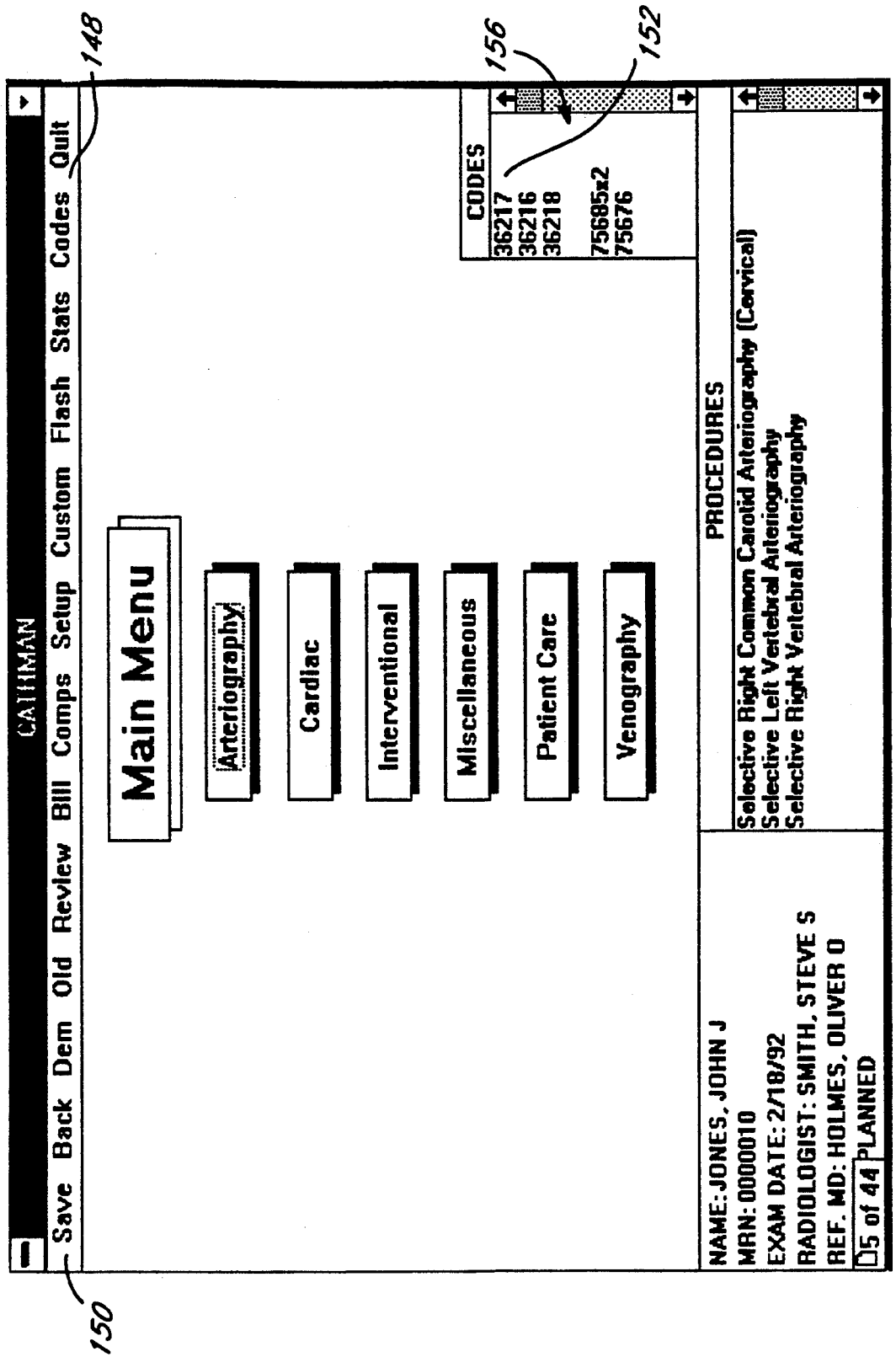
Figure 3G:
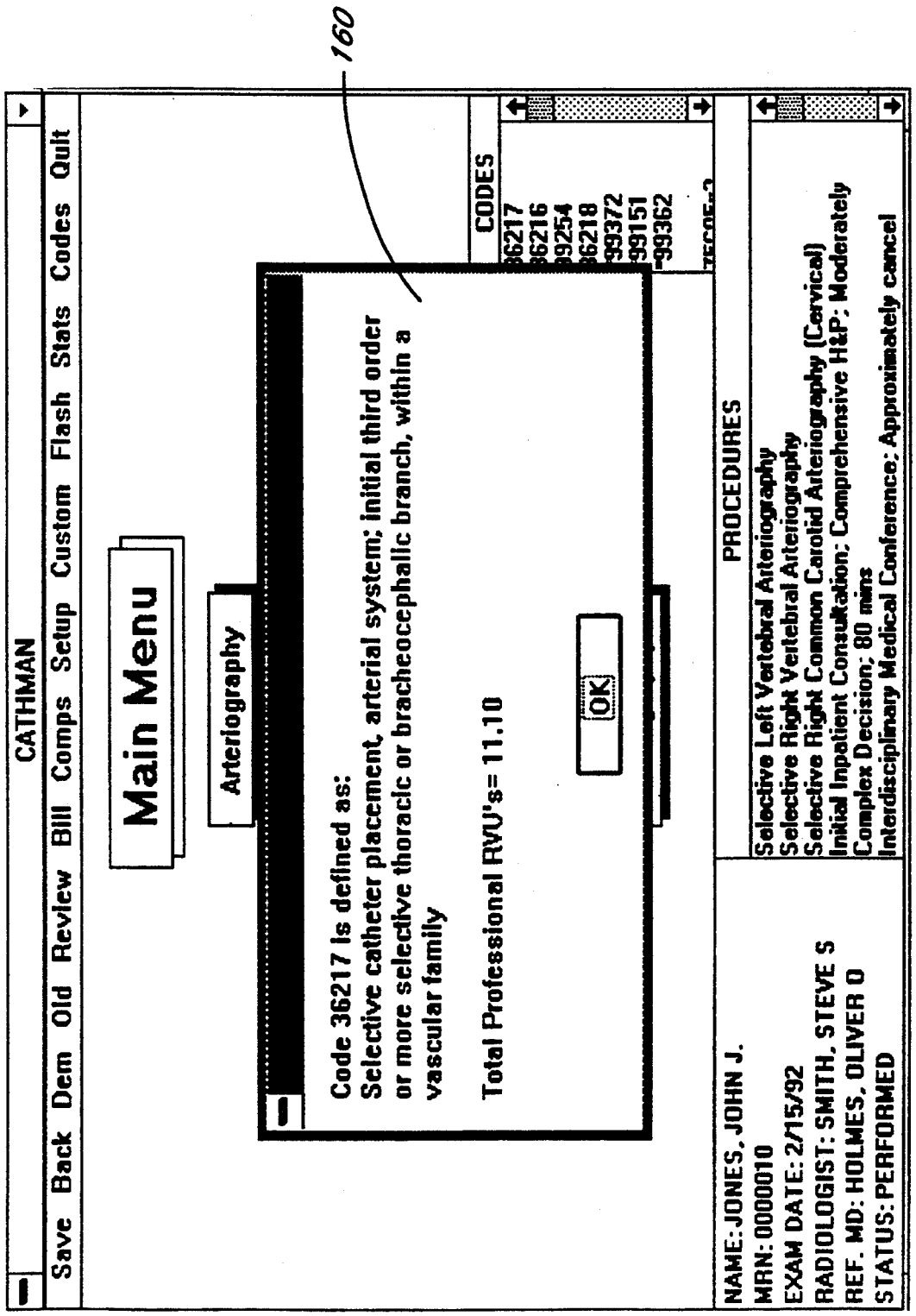

If the user returns to the Main Menu (FIG. 3A), the interactive program generates the CPT codes associated with the selected procedures, separates the codes into radiological codes and non-radiological codes, and orders the codes in descending order of RVU values within each code grouping, as illustrated in FIG. 3F. The interactive program automatically keeps track of each vascular family as well as the order of the vessel studied. When the user clicks on a button corresponding to a first order vessel, the button changes color to indicate that the vessel was studied. No additional information is required because the interactive program "knows" the vessel's family and order and can code appropriately, as described in detail below. As illustrated in FIG. 3F, the user can view the CPT codes associated with the selected procedures for the current examination by clicking on a CODES hotword 148 in the top field 150 to cause a CODES field 156 to appear. Additionally, as illustrated in FIG. 3G, if the user clicks on any CPT code 152 listed in the CODES field 156, the interactive program displays a dialogue box 160 containing the CPT code, the CPT description for that APT code and a total professional RVU value for that code. For example, FIG. 3G illustrates the dialogue box displayed by the interactive program if the user clicks on the 36217 code in the displayed CODES field 156.

FIG. 4 illustrates the branching structure of the interactive program. The structure branches from each major procedural categories into a plurality of procedural categories. In turn, each procedural category branches into a plurality of procedures indicated on the examination screens. Some procedures further require the user to enter additional parameters specific to the procedure in order to determine the appropriate CPT code.

Figure 5A:
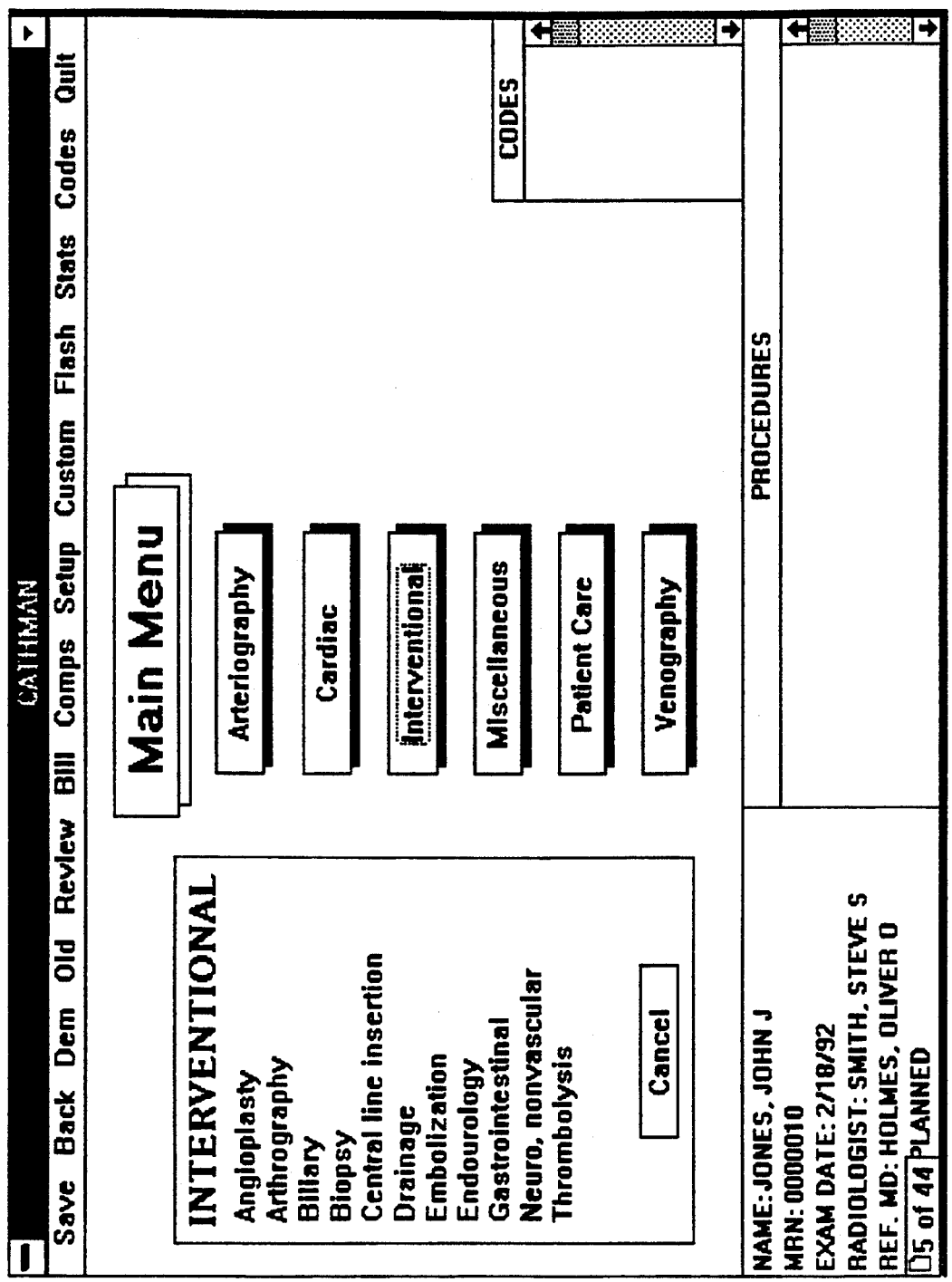
FIGS. 5A through 5G are representations of several illustrative screen displays generated by the interactive program showing examination screens and additional parameter screens.
Figure 5B:
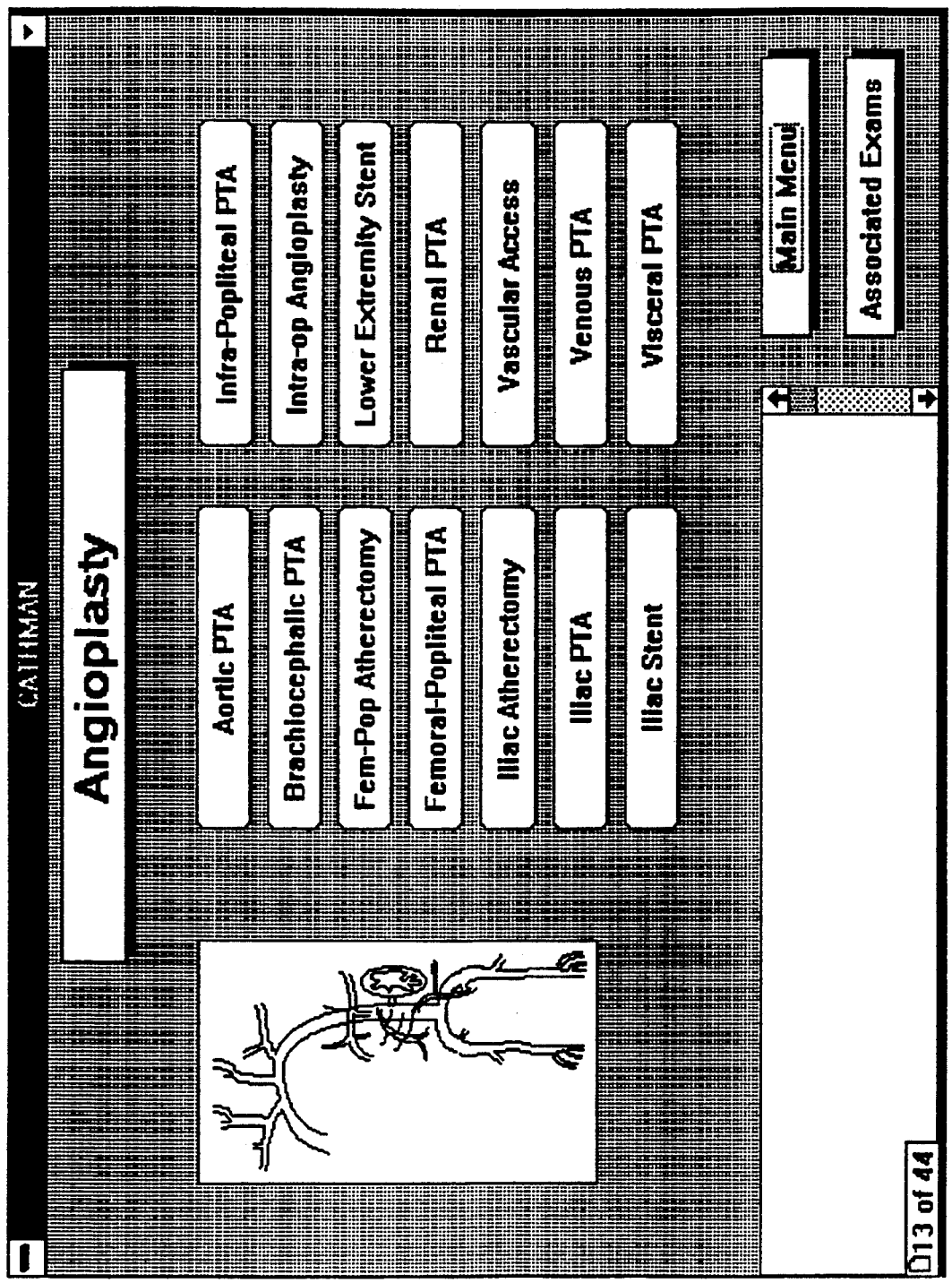
Figure 5C:
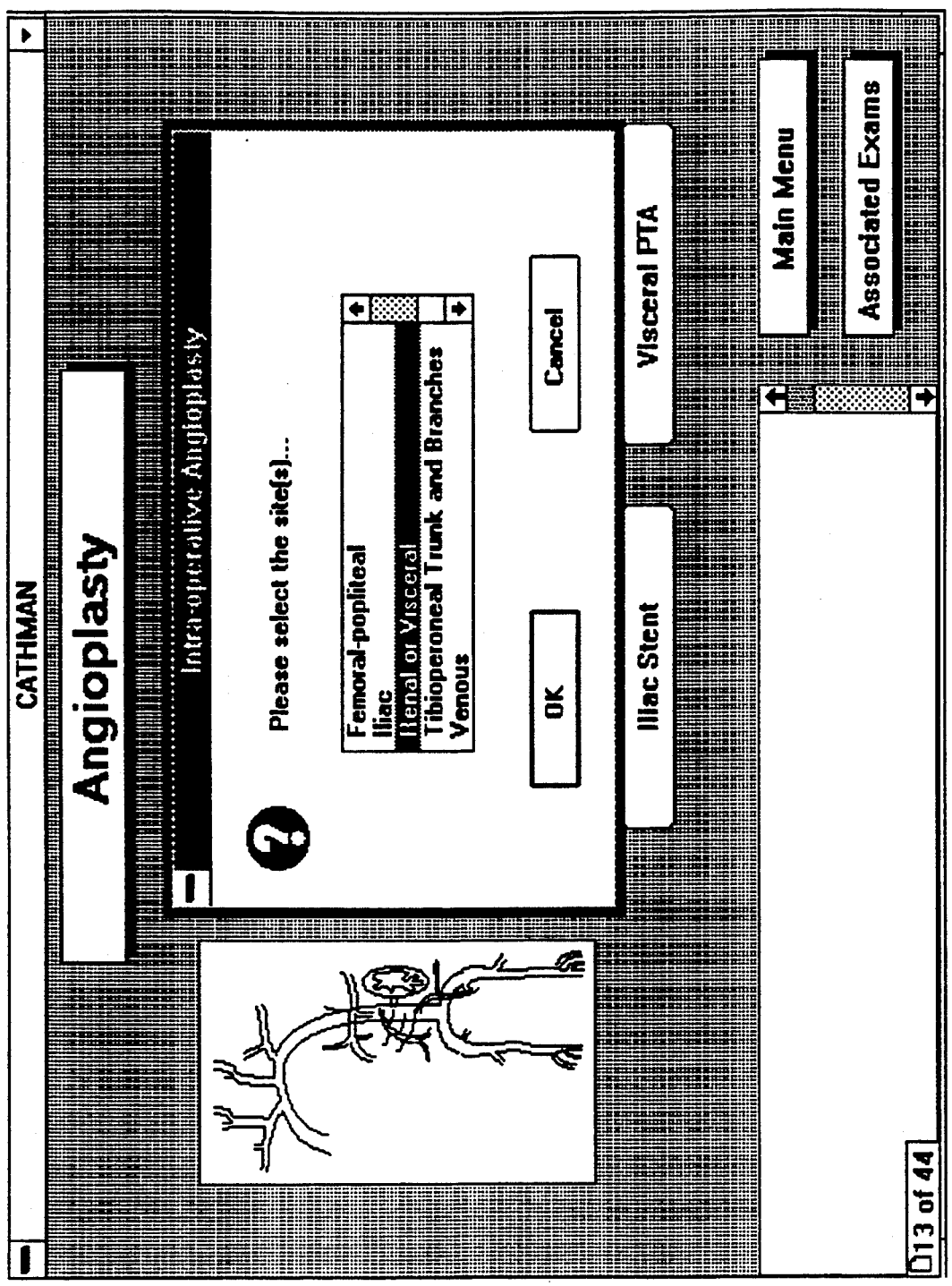
Figure 5D:
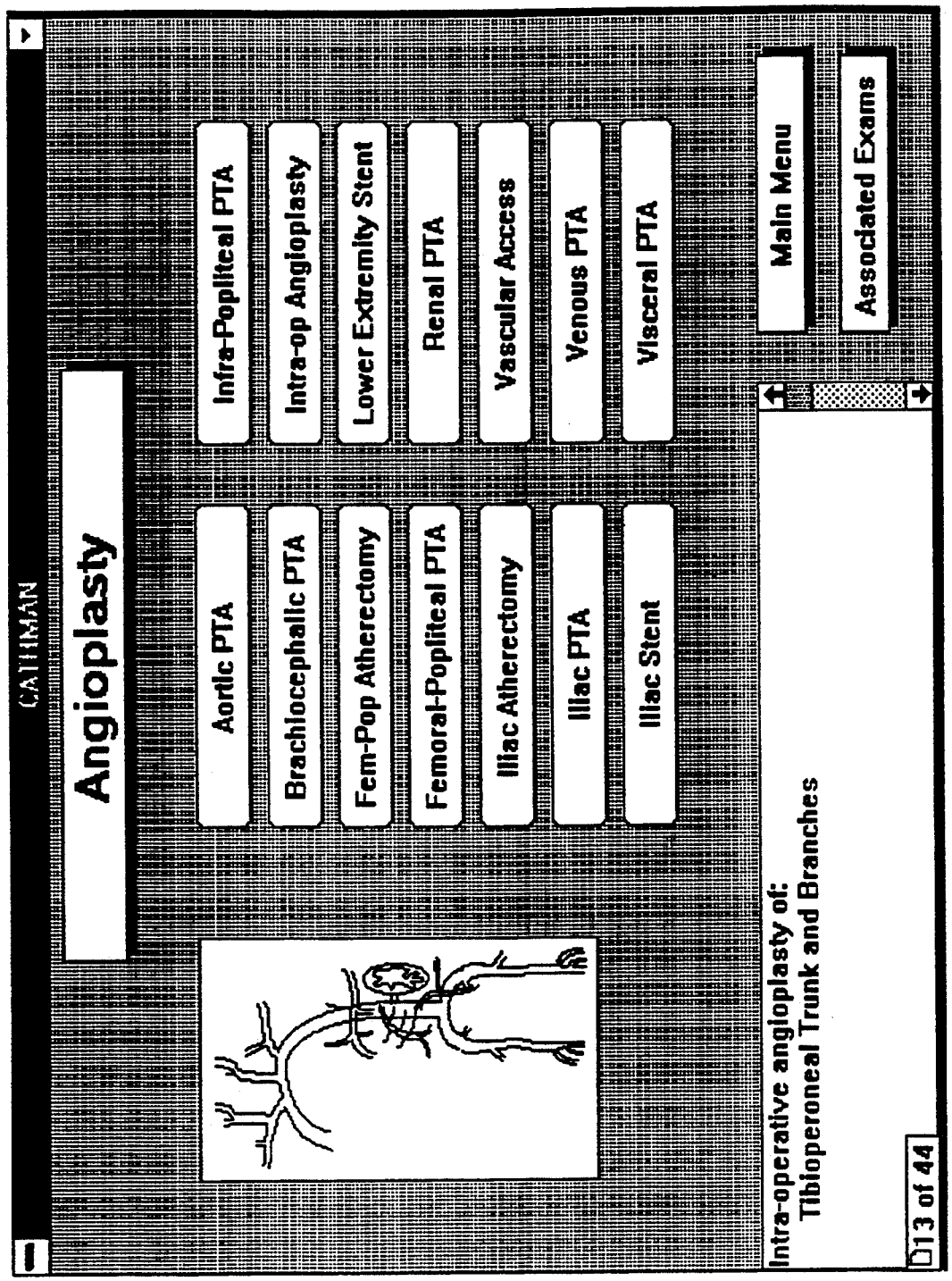

FIG. 5A through 5G illustrate another branch of the interactive program stemming from the Main Menu which requires the user to specify additional parameters before generating the corresponding CPT codes. Referring to FIG. 5A, the interactive program displays the procedural categories under the INTERVENTIONAL major category after the user has selected the corresponding button on the Main Menu. By selecting the ANGIOPLASTY hotword, the interactive program brings up the examination screen of FIG. 5B. The user can then input the procedures planned or performed by selecting the appropriate buttons. For example, a user may select the INTRA-OP ANGIOPLASTY button. As illustrated in FIG. 5C, the interactive program will then require the user to select the surgical site involved. After receiving a selection, the interactive program re-displays the examination screen with the procedure drawing highlighted and the procedures field containing the corresponding textual description, as illustrated in FIG. 5D.

Figure 5E:
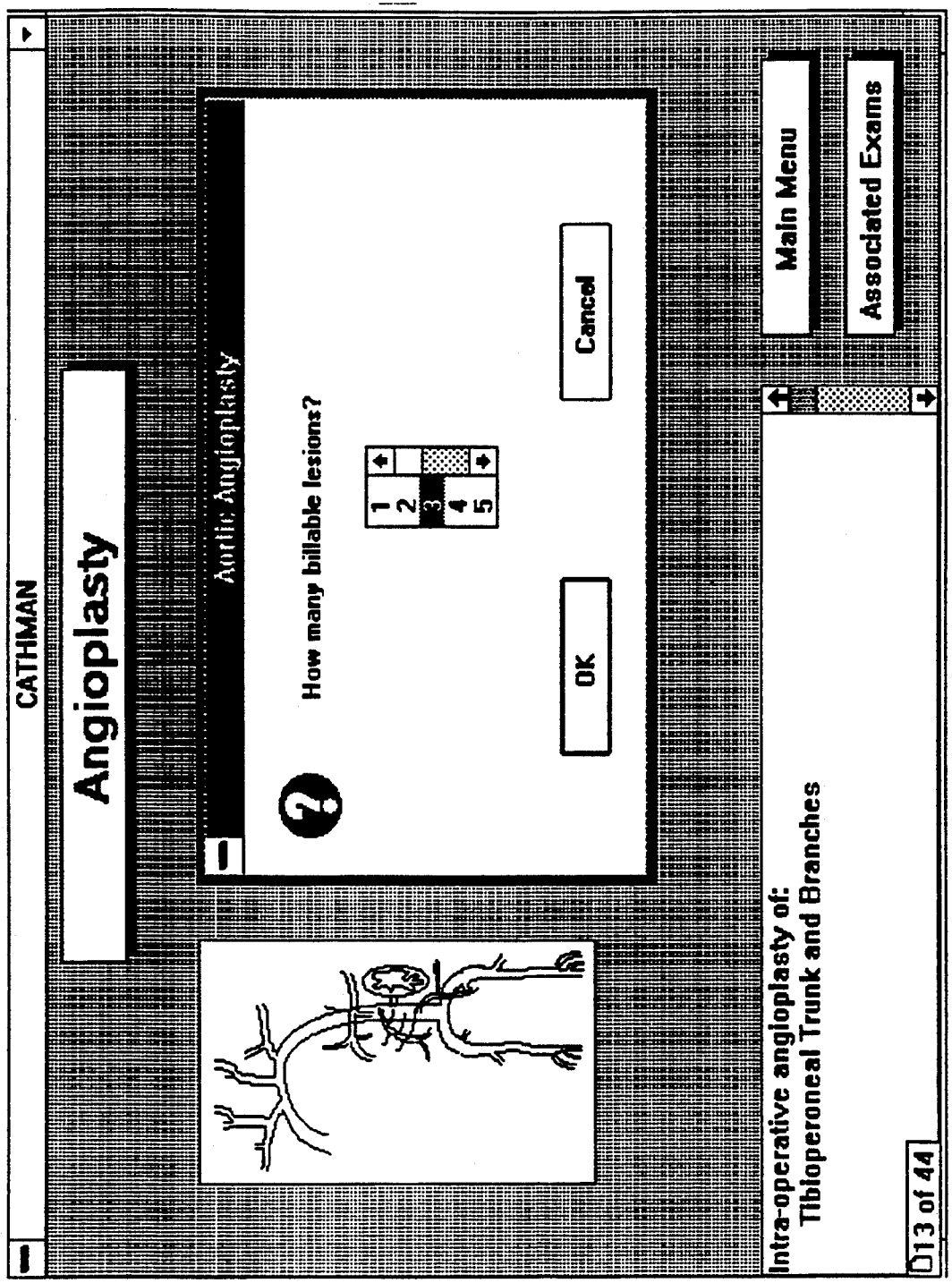
Figure 5F:
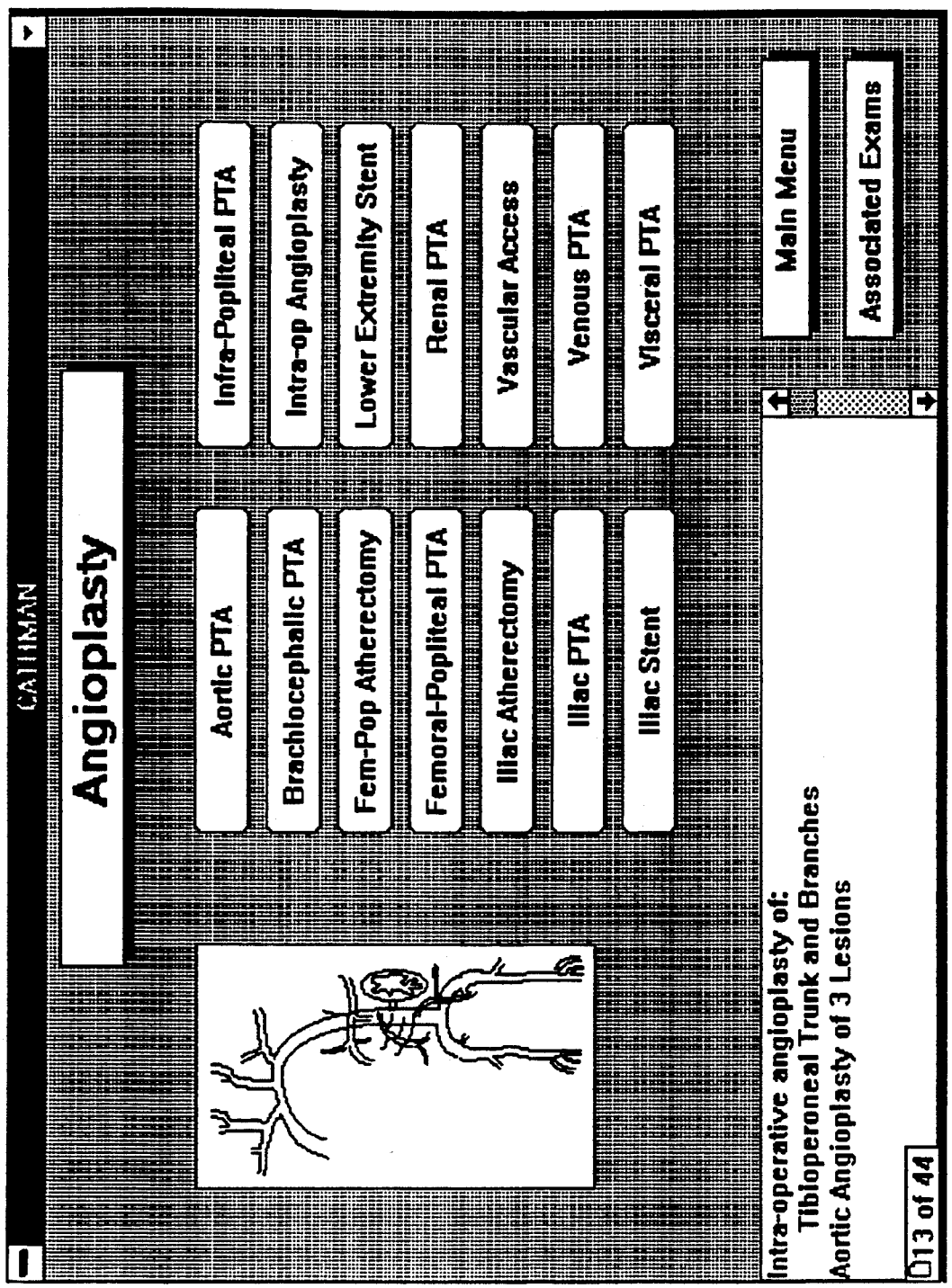
Figure 5G:
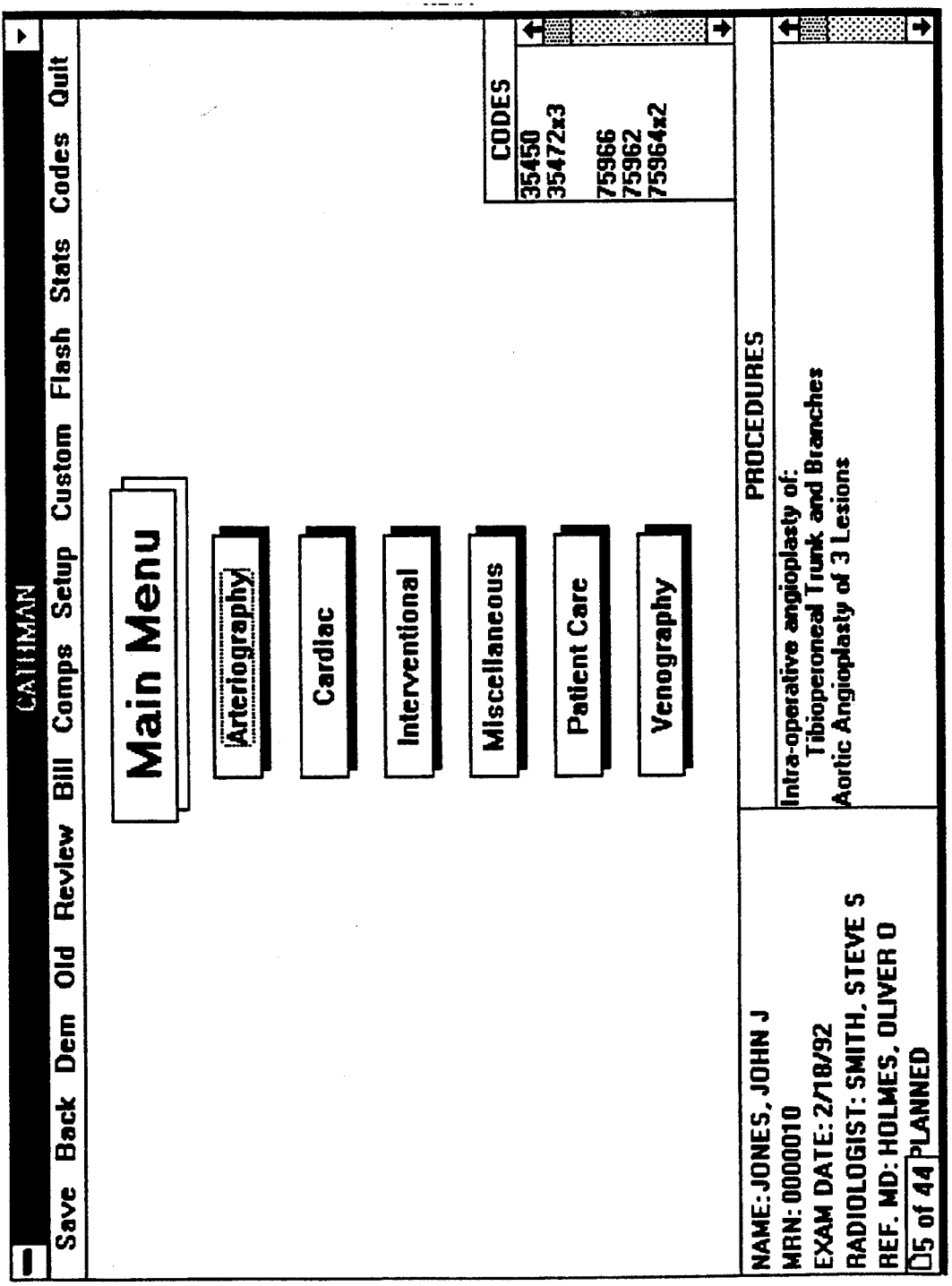

Referring to FIGS. 5D and 5E, if the user subsequently selects an Aortic Angioplasty procedure, the interactive program will require the user to indicate the number of billable lesions repaired during the procedure (or planned to be repaired). After receiving an input from the user, the interactive program re-displays the examination screen with the procedure drawing highlighted to indicate both selected procedures and the procedures field containing a textual description of both selected procedures, as illustrated in FIG. 5F. The user can then obtain the corresponding CPT codes by returning to the Main Menu and clicking on the CODES field, as illustrated in FIG. 5G.

Figure 6A:
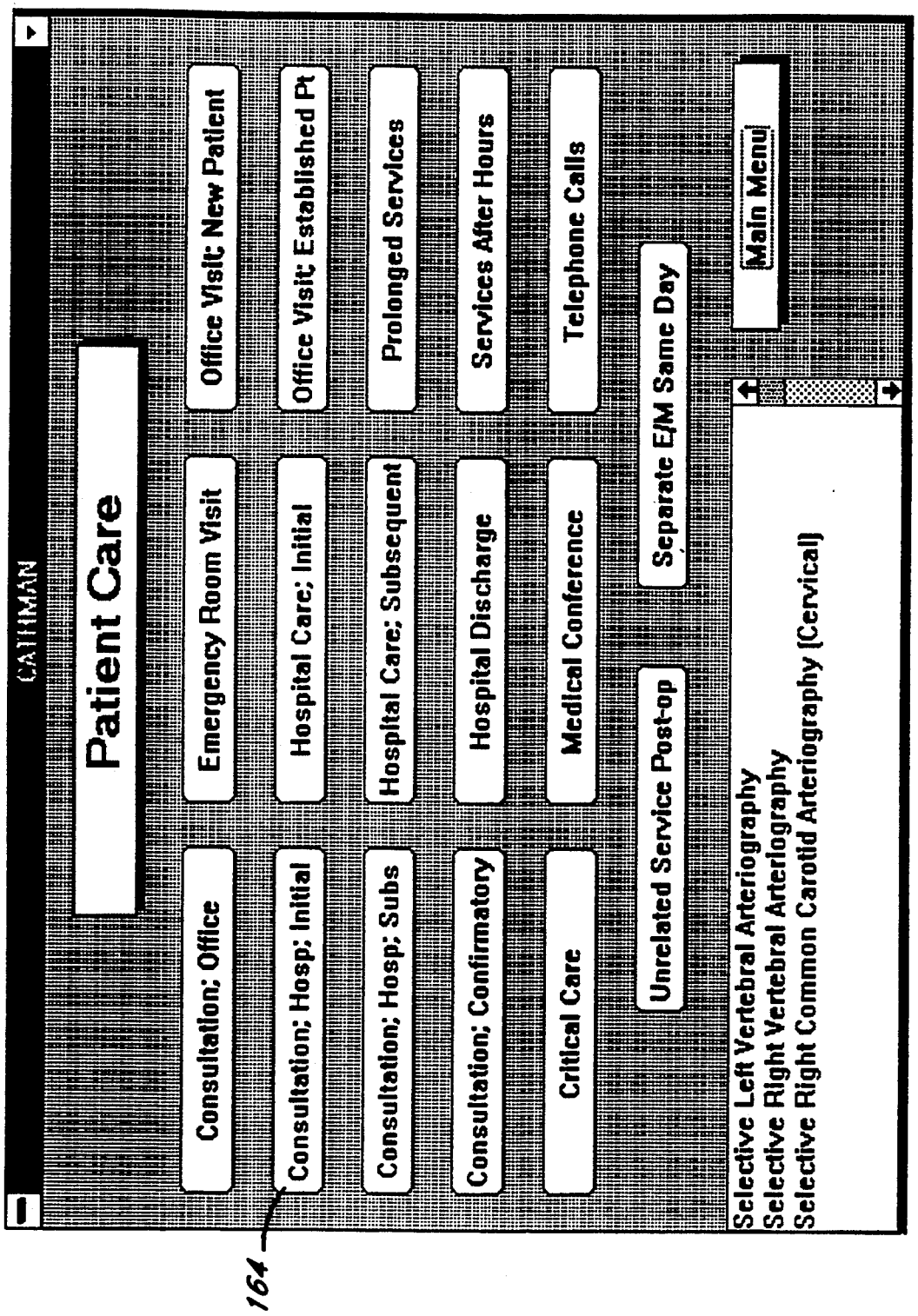
FIGS. 6A and 6B are representations of several illustrative screen displays generated by the interactive program showing additional parameter screens related to patient care.
Figure 6B:
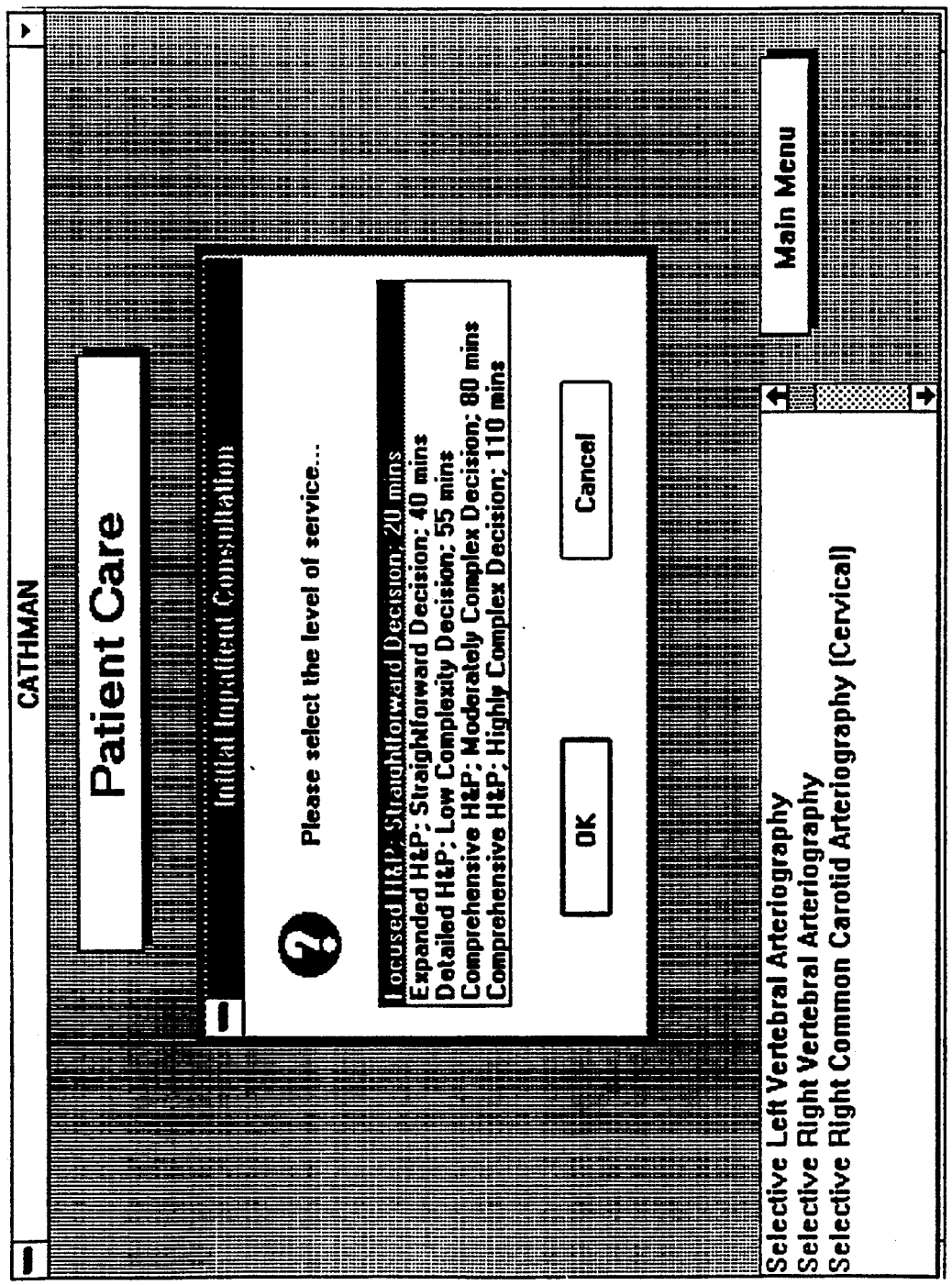
Figure 7:
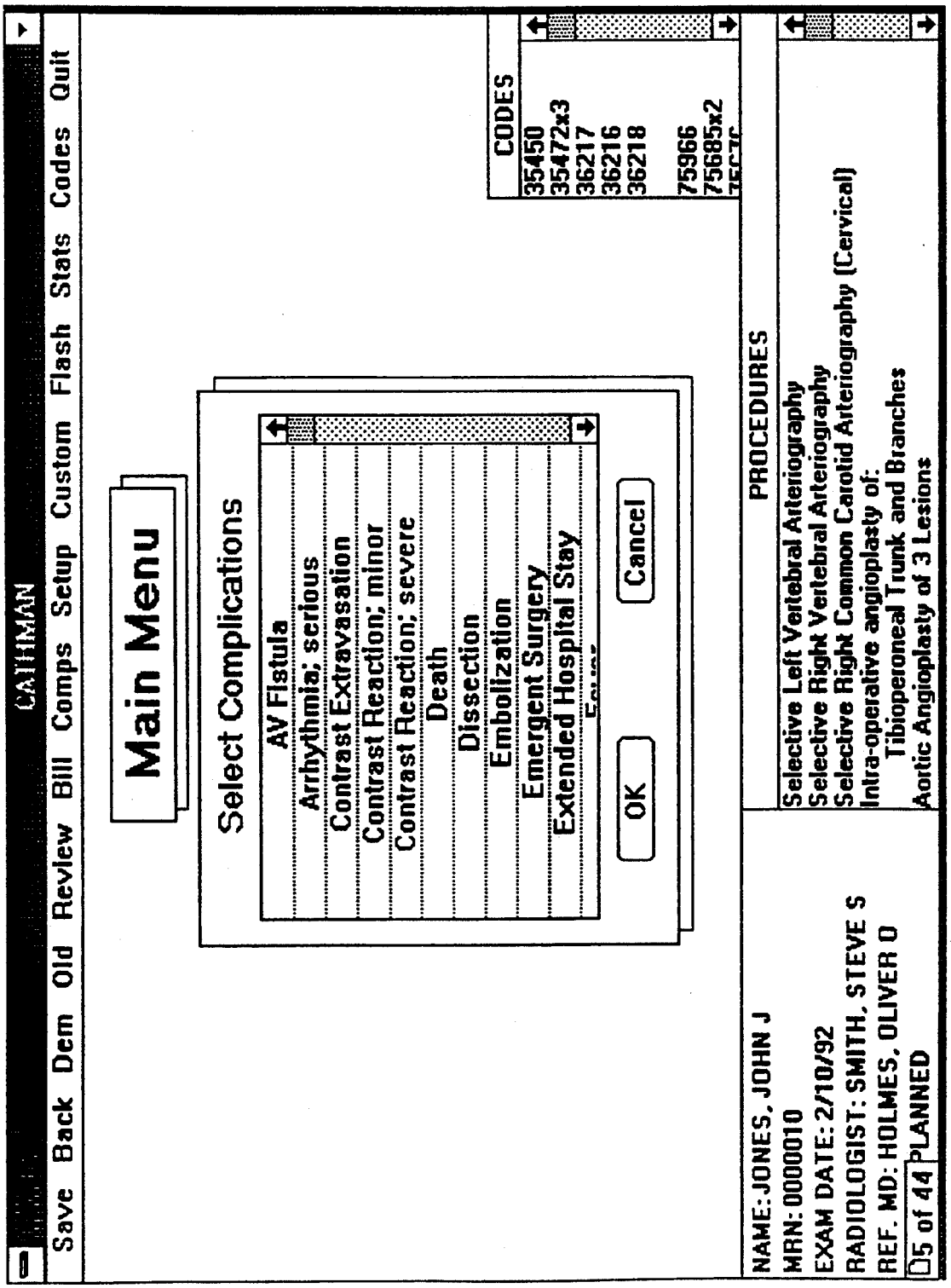
FIG. 7 is a representation of an illustrative screen display generated by the interactive program that shows a complications selection screen.

The interactive program also requires the user to input subjective parameters to determine the CPT codes for some patient care procedures. For instance, if the user selects an initial patient consultation button 164, as illustrated in FIG. 6A, the interactive program requests that the user indicate the level of difficulty in determining a diagnosis. As illustrated in FIG. 6B, the interactive program provides the user with choices of varying levels of difficulty. After receiving a selection from the user, the interactive program re-displays the examination screen illustrated in FIG. 6A.

After the user inputs all procedures planned or performed, the user can save the examination data record. To save the examination data, the user clicks on a SAVE hotword 168 in the top field 150 of the screen display, as shown in FIG. 3A. This will store the examination data on the hard disk, creating a unique examination record for the particular patient examination. If the user attempts to exit an examination before saving the data, the interactive program will remind the user to save the data before it is lost. The interactive program will then save the data or will require additional information from the user, depending upon the "status" of the examination record.

The interactive program assigns one of the following statuses to each examination: PLANNED, PERFORMED, REVIEWED and BILLED. The user enters PLANNED examinations on or before the date of the examination, which can commonly be done by clerical personnel based on information received from the initial appointment conversation or from an X-ray requisition. The PLANNED status allows the radiologist to keep track of future examinations and to reduce the amount of data entered after the radiologist has performed the examination.

Referring to FIG. 3A, the Main Menu includes a data field 172 containing, among other information, the status of the examination record. If the data entered contains a future examination date, the interactive program assigns a PLANNED status to the examination record. The interactive program also assigns a PLANNED status to the examination record if the date entered is a previous examination date. However, the interactive program asks if user wants to update the status to PERFORMED before saving the examination record to the hard disk at the end of the session. Additionally, the user can switch a PLANNED status to a PERFORMED status, and vise versa, by clicking on the STATUS hotword 176 in the data field 172 during the program.

The user typically recalls the examination record after the radiologist has performed the examination, and modifies the data, if necessary, to reflect what procedures the radiologist actually performed. Once the user reviews a planned examination record, the interactive program asks if the user wants to update the status to PERFORMED before saving the examination record to the hard disk. The user can also change the status of the examination by clicking on the STATUS hotword 176 as discussed above.

When an examination is first saved with the status of PERFORMED, the interactive program asks the user the following questions: "Was the patient an outpatient or an inpatient?"; "Was the examination a success?"; "Was the examination a teaching case?"; "Were there any complications associated with the examination?" If the user answers the last question "yes," the interactive program displays a list of complications, as illustrated in part in FIG. 7. The user can select any number of items on the list by clicking on those particular items. Additionally, the user can enter specific data regarding complications not enumerated by the list.

Figure 8A:
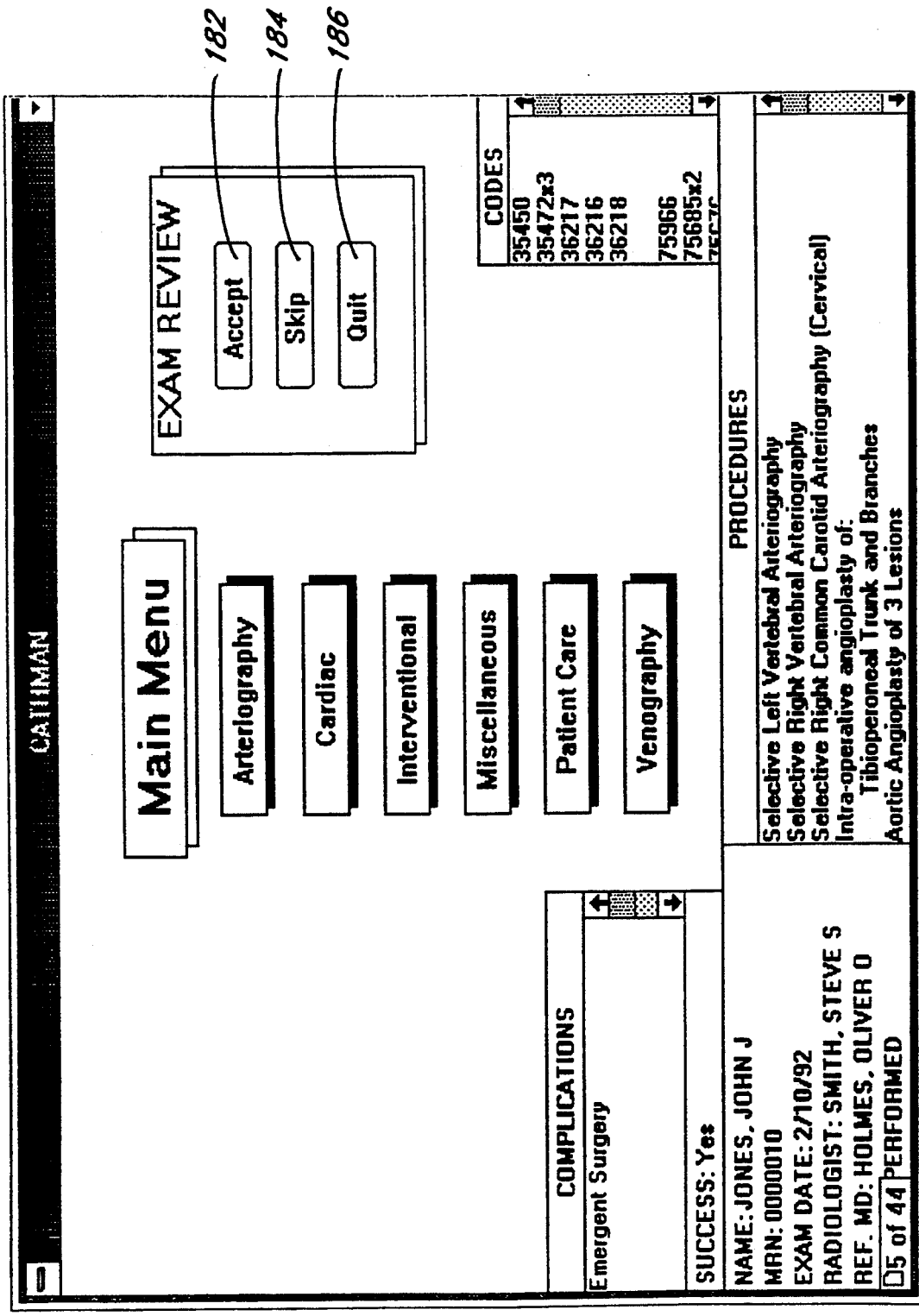
FIGS. 8A and 8B are representations of illustrative screen displays generated by the interactive program that show several screens used with a review feature.

Referring to FIGS. 3A and 8A, when the user clicks a REVIEW hotword 180 in the top field 150, the interactive program searches for all performed examinations and displays the review screen, as illustrated in FIG. 8A. For each examination, the review screen shows the patient's name and medical record number, the examination date, the name of the radiologist and of the referring physician, the examination status (always performed), and the selected procedures with their associated CPT codes.

The REVIEW function allows the user to quickly review all performed examinations before billing the examinations. The interactive program recalls all performed examinations in a batch to allow rapid review of multiple examinations. The user can review, modify and approve the performed examination data during a single review step.

The REVIEW function is one of the most important features of the interactive program. The level of reimbursement from interventional billings is often related to the degree of participation in the billing process by the interventional radiologist. Because most interventional radiologists have little time for billing chores, the REVIEW function is designed to let the interventional radiologist put maximum input into procedure coding in a minimum amount of time.

As illustrated in FIG. 8A, the review screen contains three buttons: ACCEPT button 182, SKIP button 184 and QUIT button 186. The user clicks the ACCEPT button 182 when the user determines that an examination is correct as displayed and the user wants to save the examination with a status of REVIEWED. After an examination status changes to REVIEWED, it is ready to be billed.

If the user clicks on the SKIP button 184, the interactive program displays a new patient examination for review without altering the performed status of the skipped examination. Any changes made by the user during the review function to an examination later skipped, will not be saved; the skipped examination is left intact, as if it had never been reviewed.

If the user clicks on the QUIT button 186, the interactive program exits the review function. All performed examinations which the user did not review or which the user skipped would remain unchanged.

Figure 8B:
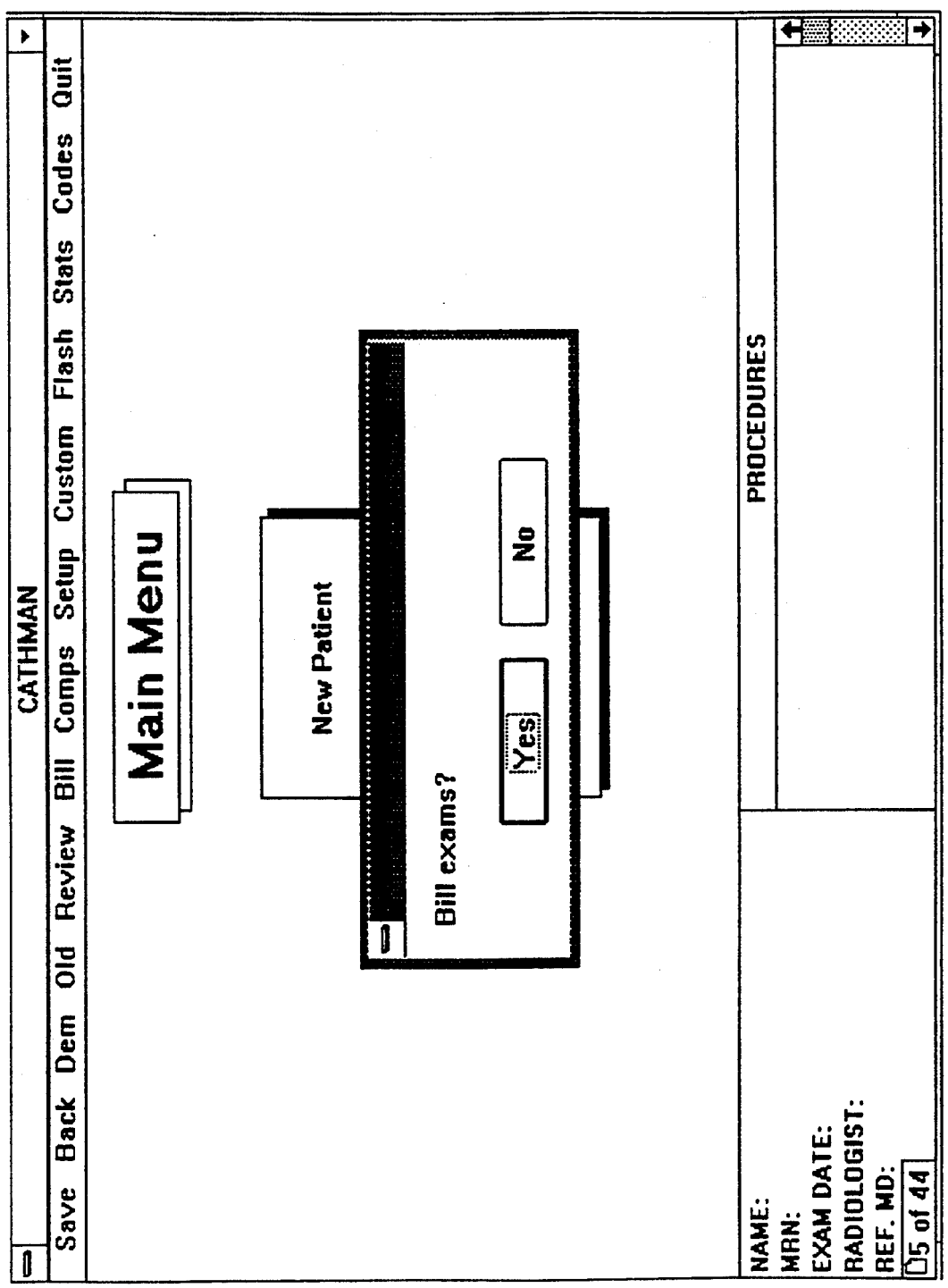

After the user reviews the performed examinations, the status of the examinations changes from PERFORMED to REVIEWED. The interactive program also asks the user if the reviewed examinations should be billed, as illustrated by FIG. 8B.

When reviewed examinations are billed, all examinations which have been coded by the interactive program and reviewed by the user are sent to the billing office within the radiologist's practice. Billing reports can be sent using sheets of paper printed on a printer or via comma-delimited ASCII files that are placed on a hard drive or floppy disk. After an examination is sent to the billing office, the status changes to BILLED.

Referring to FIG. 3A, the Main Menu also contains a plurality of hotwords in the top field 150, a number of which have been previously described. The BACK hotword 188 allows the user to skip back a stage in the entry of examination data. The DEM hotword 190 displays the demographics for the patient of the open examination file. Clicking on the OLD 192 hotword brings up all examination files with a planned status but with an examination date prior to the current date. Clicking on COMPS 194 allows the user to view, modify or enter complications in the open examination file. The CUSTOM hotword 196 lets the user enter custom codes for specific procedures. The SETUP hotword 197 lets the user set up parameters used by the interaction program. Clicking on FLASH 198 turns off the flashing function of lower level screens. Finally, clicking on the STATS hotword 199 takes the user to the statistics screen of the interactive program. The interactive program preferably contains statistical features to track complicated cases, cases for each radiologist, cases by particular CPT codes, etc. The hotwords provide the user with easy access to these features of the interactive program.

The interactive program generates the appropriate CPT codes associated with the procedures and procedure parameters input by the user by implementing a series of method steps comprising a final common pathway. An exemplary flow chart of an initial sequence of selecting a patient examination record and of the final common pathway in accordance with the present invention is illustrated in FIGS. 9A through 9J.

Figure 9A:
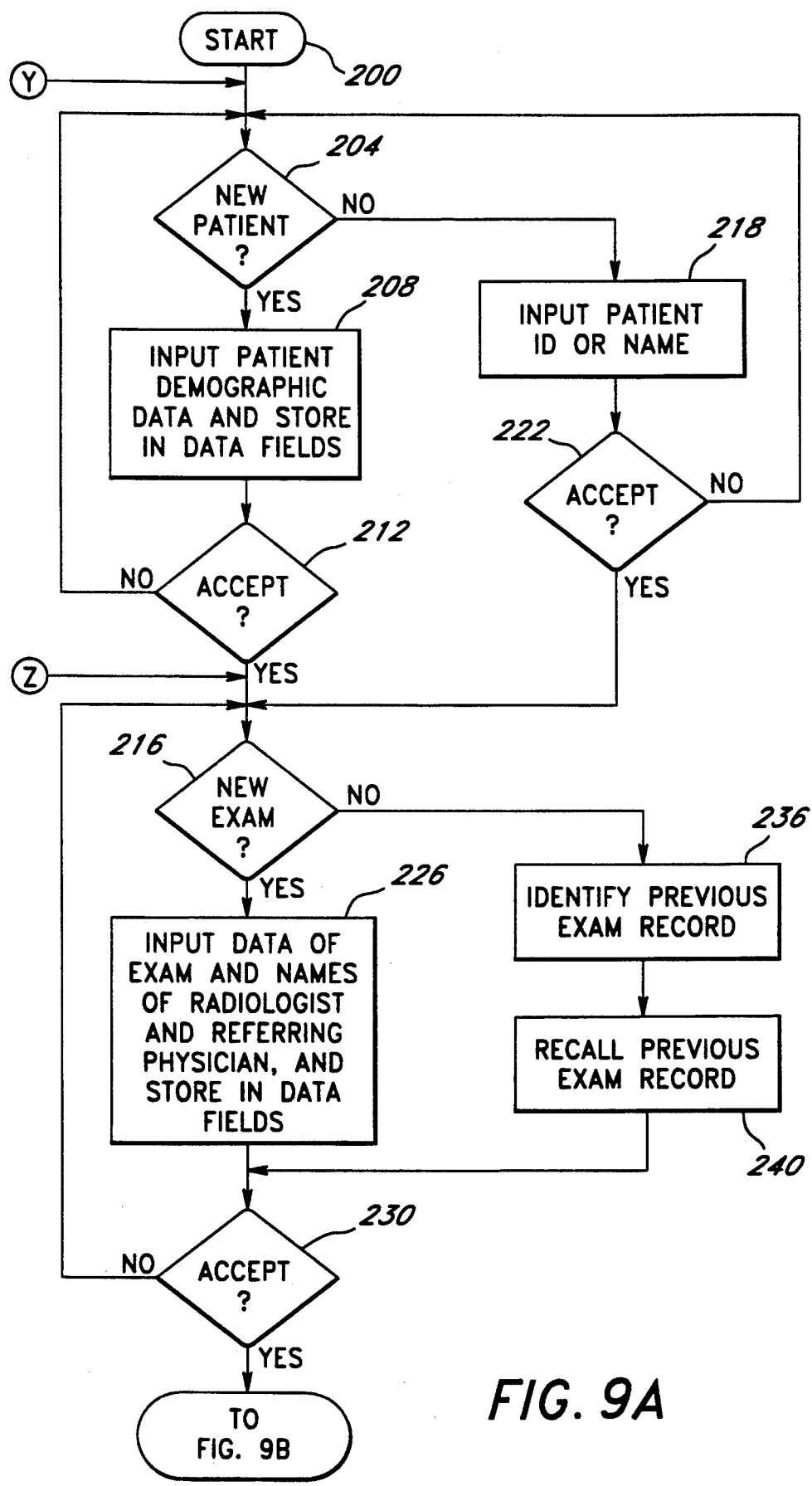
FIGS. 9A through 9J illustrate a flow diagram of the interactive program embodying the present invention.

Referring to FIG. 9A, the interactive program begins at the START block 200 and proceeds to a first decision block 204 where the interactive program responds to the users selection between a new patient and a previous patient. FIG. 2A illustrates the initial screen display generated by the interactive program requesting the user to make this selection. Referring back to FIG. 9A, if the user selects a new patient, the interactive program proceeds to an activity block 208 and receives patient demographics data input by the user. The interactive program then proceeds to a decision block 212 where the interactive program requests the user to accept the entered patient demographics data. If the user accepts the entered data, the interactive program creates a patient file and stores the patient demographics data to a specific system variable 214 (FIG. 1). The interactive program then proceeds to a decision block 216. If the user does not accept the entered data, the interactive program returns to the preceding decision block 204.

Referring to FIG. 1, as used herein, the term "system variable 214" refers to a section of RAM memory of the computer platform 104 which is accessible by the interactive program at any stage, "memory field 219" refers to nonvolatile memory location of a data storage system, such as, for example, a hard disk drive (i.e., a Winchester drive), and "local variable 220" refers to a section of RAM memory of the computer platform 104 which is accessible by the interactive program only during specific routines.

Returning to the first decision block 204, if the user selects a previous patient, the interactive program proceeds to an activity block 218 and requests that the user enter the desired patient's name or medical identification number, as illustrated in FIG. 2C. Referring back to FIG. 9A, the interactive program then proceeds to a decision block 222 where the interactive program requests the user to accept the entered patient identification data. If the user accepts the entered data the interactive program retrieves the selected patient file and proceeds to the decision block 216. If the user does not accept the entered data, the interactive program returns to the initial decision block 204.

After determining a specific patient file, the interactive program proceeds to the following decision block 216 to select a particular examination record. The interactive program responds to the user's selection between a new examination and a previous examination. FIG. 2E illustrates the screen display generated by the interactive program requesting the user to make this selection.

Figure 9B:
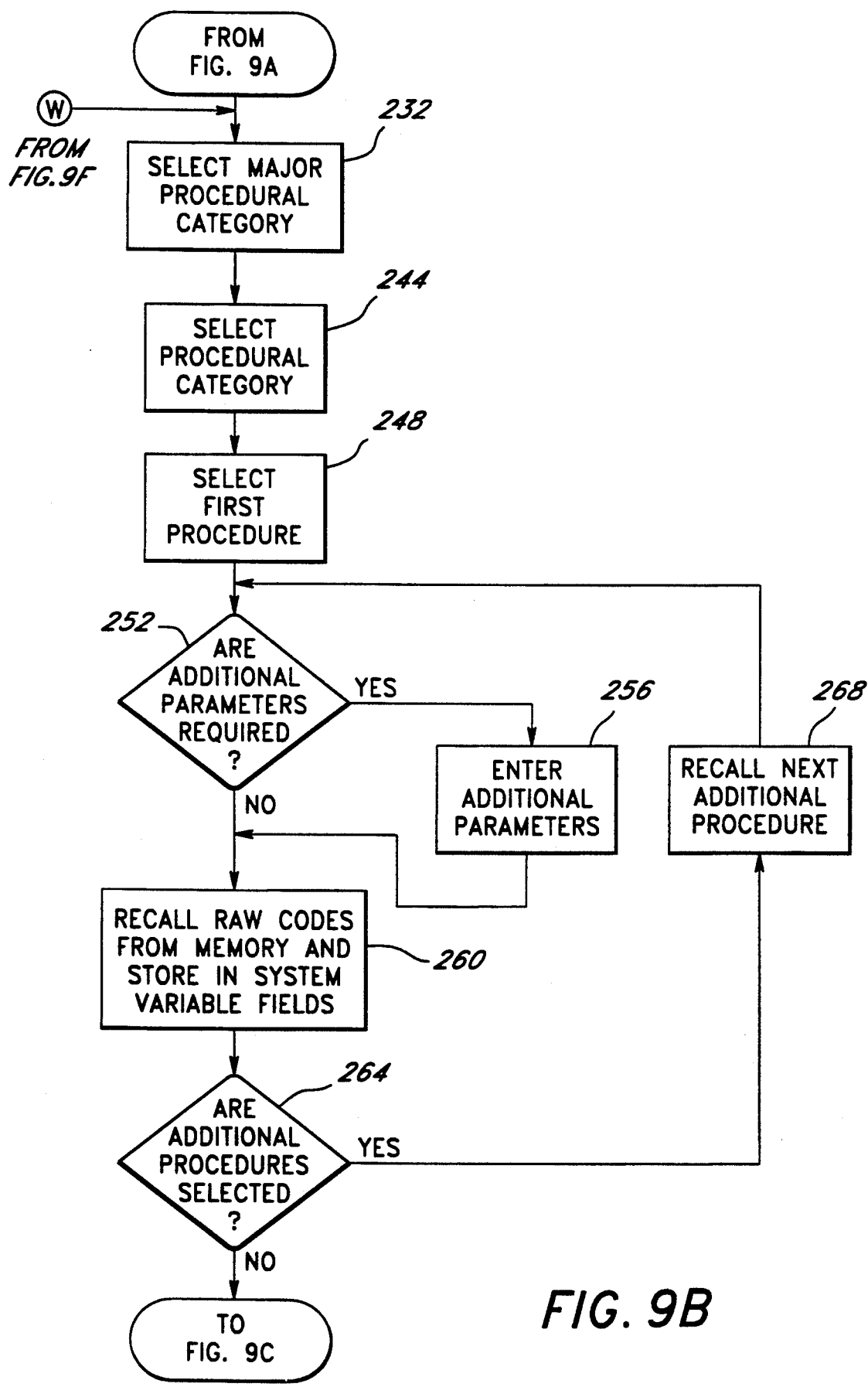

Referring back to FIG. 9A, if the user selects a new examination, the interactive program proceeds to an activity block 226 and receives demographic data input from the user concerning the radiologist and the referring physician. The interactive program then proceeds to a decision block 230 where the interactive program requests the user to accept the entered demographic data. If the user accepts the entered data, the interactive program stores the name of the radiologist and referring physician in a system variable. The interactive program also stores the demographic data of the radiologist and referring physician to a memory file. The interactive program then proceeds to a decision block 232 (FIG. 9B). If the user does not accept the entered data, the interactive program returns to the decision block 216.

Returning to the decision block 216, if the user selects a previous examination record, the interactive program recalls all examination files within the selected patient's file. The interactive program then proceeds to an activity block 236 and requests that the user select the desired examination, as illustrated by the screen display in FIG. 2J. After determining the specific examination record, the interactive program proceeds to an activity block 240 where the interactive program recalls the previous examination record and proceeds to the activity block 232 (FIG. 9B).

After determining the specific examination record, the user enters the procedures that where involved during the patient examination. Specifically, the user selects between the major procedural categories illustrated by the screen display of FIG. 3A. Referring to FIG. 9B, the interactive program receives the user's selection at the activity block 232 and proceeds to an activity block 244 where the interactive program receives the user's selection of the specific procedural category (FIG. 3B). After receiving the specific procedural category, the interactive program displays an examination screen containing procedural selections for the user and proceeds to an activity block 248. When the user selects a first procedure, the interactive program advances to a decision block 252 where the interactive program decides if any additional parameters are required to determine the raw code associated with the selected procedure. As used herein, "raw code" refers to a string of numeric and alphanumeric characters which act as a low level code between the selected procedure and the associated CPT code. An "intermediate code" refers to a code that is generated from manipulating the raw code by the steps of the final common pathway. A "final code" refers to the CPT code associated with the selected procedures. If additional parameters are required to determine the raw code associated with the selected procedure, the interactive program proceeds to an activity block 256 and requests the user to enter the required additional parameters. Examples of requests for additional parameters are illustrated by the screen displays of FIGS. 5C, 5E, and 6B. From the activity block 256, the interactive program advances to an activity block 260.

Returning to the decision block 252, if additional parameters are not required to determine the associated raw code, the interactive program proceeds to the activity block 260. The interactive program then recalls the raw codes associated with the selected examination from memory and stores the raw codes in the following designated system variables 214 (FIG. 1): X-Ray, X-Ray2, Surgical, and a series of vascular families (vascular family X, where X=1 through Y, and Y represents the number of vascular families monitored by the interactive program).

After storing the raw codes associated with the first procedure selected, the interactive program advances to a decision block 264 to decide if the user has selected any additional procedures. If the user has selected another procedure, the interactive program proceeds to an activity block 268 where the interactive program recalls the next procedure selected by the user and returns to the decision block 252 to decide if any additional parameters are required to determine the raw code associated with the selected additional procedure. The interactive program repeats this routine until it has stored the raw codes for all selected procedures in the designated system variables 214 (FIG. 1).

Figure 9C:
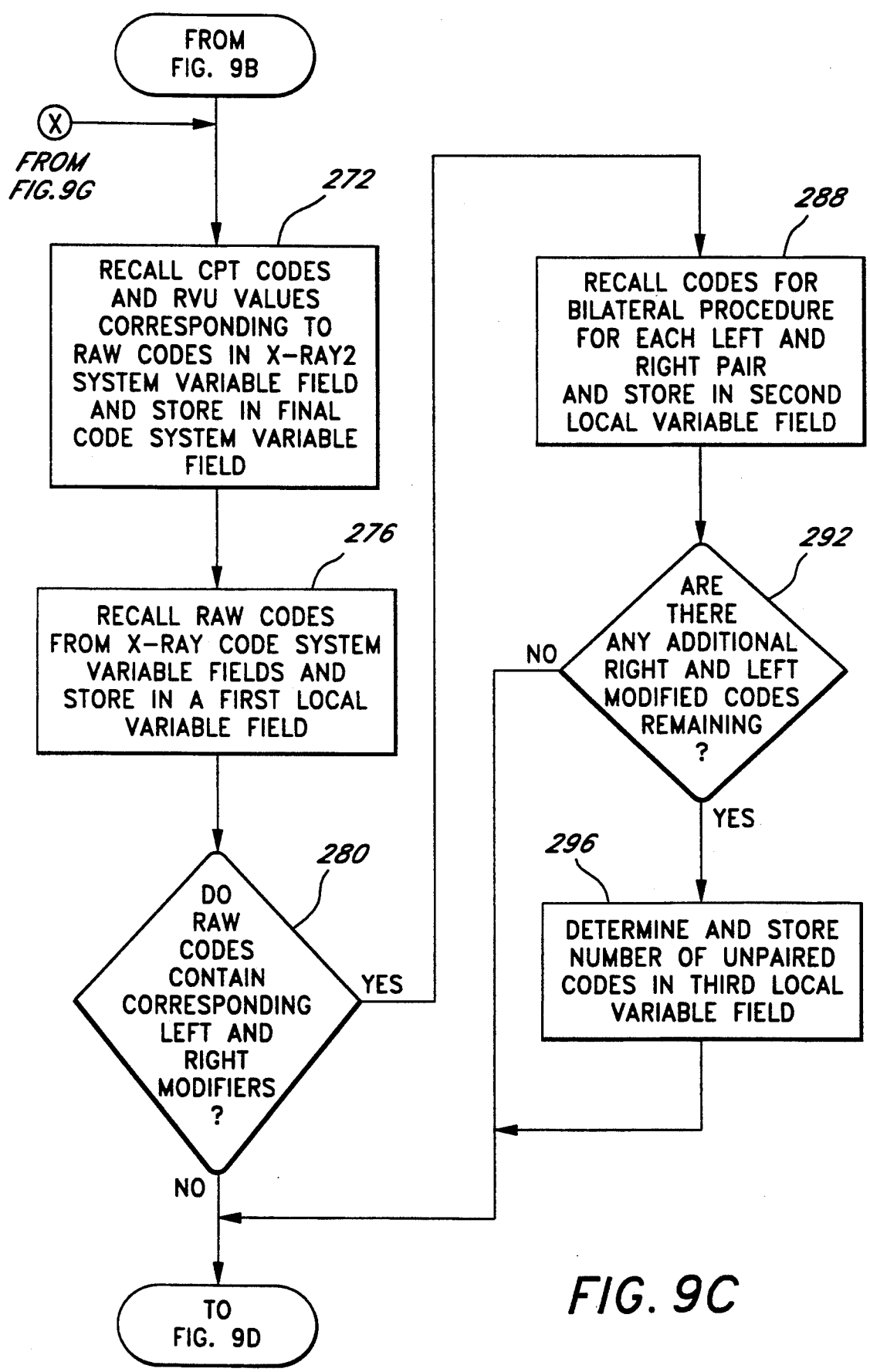

Referring to FIG. 9C, after determining the raw codes associated with the selected procedures, the interactive program runs through a final common pathway when the user returns to the Main Menu (FIG. 3A) from an examination screen (e.g., FIG. 3C). The interactive program proceeds from the decision block 264 to an activity block 272 where it recalls the CPT codes and RVU values from memory corresponding to the raw codes stored in the X-Ray2 system variables (FIG. 1). After retrieving the associated CPT codes and RVU values, the interactive program stores the CPT codes and RVU values in a final code system variable. Specifically, the interactive program stores the CPT code and corresponding RVU value together in one string of numeric characters with the first five digits from the left representing the RVU value and the last five digits from the left representing the associated CPT code. The interactive program clears the final code system variable before performing the step indicated by the activity block 272 each time the interactive program runs through the final common pathway.

Although the following description of the final common pathway describes the interactive program as placing the intermediate codes (i.e., the RVU value and CPT code string) in the Final Code system variable and then acts upon those codes to generate the CPT codes displayed in the screen code field 156, it is understood that the interactive program could alternatively place the intermediate codes first in a local variable, act upon the codes and then place the final codes in a ranked order into the Final Code system variable.

The interactive program then advances to an activity block 276 where it stores the raw codes in the X-Ray code system variable in a first local variable 220 (FIG. 1). In this manner, the interactive program can manipulate the raw codes without losing track of the original raw codes. As discussed in detail above, the appropriate CPT codes may depend on the combination of procedures performed. The interactive program therefore keeps track of the raw codes associated with each selected procedure in the system variables 214, and then determines how the procedures interact in local variables 220. As a result, the interactive program generates the CPT codes associated with the selected grouping of procedures as the user adds and/or deletes procedures.

After storing the raw codes in the X-Ray local variable 220, the interactive program proceeds to a decision block 280 to determine whether the raw codes contain any corresponding right and left modifiers. That is, the interactive program determines whether the raw codes contain any identical numeric values (e.g., 75722) with an "R" and an "L" modifier. If the raw codes do not contain corresponding right and left modifiers, the interactive program proceeds to a decision block 284 (FIG. 9D).

If, however, the raw codes contain corresponding right and left modifiers, the interactive program advances to an activity block 288 where it recalls a code for the corresponding bilateral procedure (e.g., 75724) and stores the code in a second local variable 220. The interactive program then proceeds to a decision block 292 to determine whether the raw codes in the first local variable contain any unpaired right or left modified codes corresponding to the paired code. For example, if the raw codes contain three R75722 codes and one L75722 code, the interactive program would determine that two R75722 codes were remaining which would correspond to the paired codes (i.e., one R75722 code and one L75722 code). If the interactive program determines that the remaining raw codes contain additional codes with right and left modifiers, the interactive program proceeds to an activity block 296 and determines the number of additional codes (two in the above example) which it stores in a third local variable 220. The interactive program then advances to the decision block 284 (FIG. 9D).

Figure 9D:
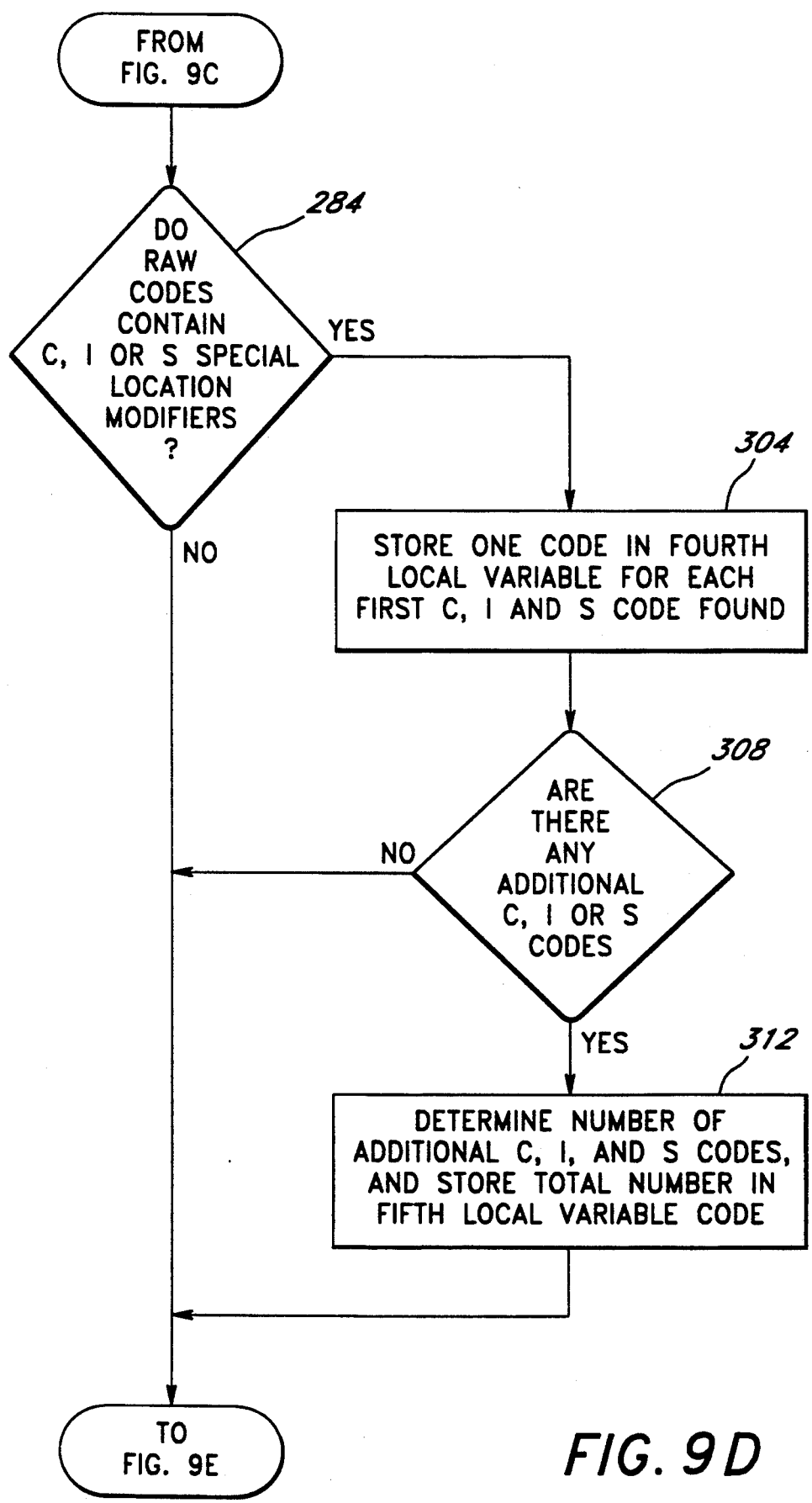

Returning to the decision block 292, if the interactive program determines that the raw codes do not contain any unpaired right and left modified codes, the interactive program proceeds straight to the decision block 284 (FIG. 9D).

Referring to FIG. 9D, the interactive program at the decision block 284 determines whether the raw codes contain any special location modifiers, for example, any C, I, or S modifiers (indicating the celiac, inferior mesenteric and superior mesenteric arteries). The special location modifiers represent areas in the CPT code which do not accurately account for the procedures performed in specific anatomic locations. For instance, the CPT codes lump together the radiological codes for arteriography of the mesenteric arteries. However, if the radiologist studies the celiac, superior mesenteric (SMA) or inferior mesenteric (IMA) arteries, the radiologist should charge separate fees for the examination of each vascular family of the mesenteric arteries. Thus, the C, S and I modifiers break down the CPT code associated with the mesenteric arteries to account for studies of individual vascular families. If the raw codes do not contain a special location modifier, the interactive program proceeds to an activity block 300 (FIG. 9E).

If, however, the raw codes contain special location modifiers, the interactive program advances to an activity block 304 where it determines if the raw codes contain one of any special location modifier. For example, the interactive program reviews the raw codes in the first local variable to determine if a C modifier exists, if an S modifier exists and if an I modifier exists. The interactive program then recalls a code for the examination of a special location (e.g., the mesenteric) and stores that code in a fourth local variable by the number of first special location modifier found. That is, continuing with the above example, if the interactive program finds three C modifiers, two S modifiers and no I modifiers, the interactive program would store the code associated with the mesenteric examination (e.g., 75726) in the fourth local variable two times; one for the first C modifier it finds and one for the first S modifier it finds.

After storing codes in the fourth local variable, the interactive program proceeds to a decision block 308 where it determines if the raw codes contain any additional special modifiers to the first special modifiers. If the interactive program determines that additional modifiers exist, the interactive program advances to an activity block 312 where it determines the total number of additional special location modifiers. For instance, in the above example, the interactive program examines the raw codes and determines that the raw codes in the first local variable contain two additional C modifiers and one additional S. The interactive program then stores the total number of additional specific location modifiers (three in the above example) in a fifth local variable. The interactive program then proceeds to the activity block 300 (FIG. 9E).

Figure 9E:
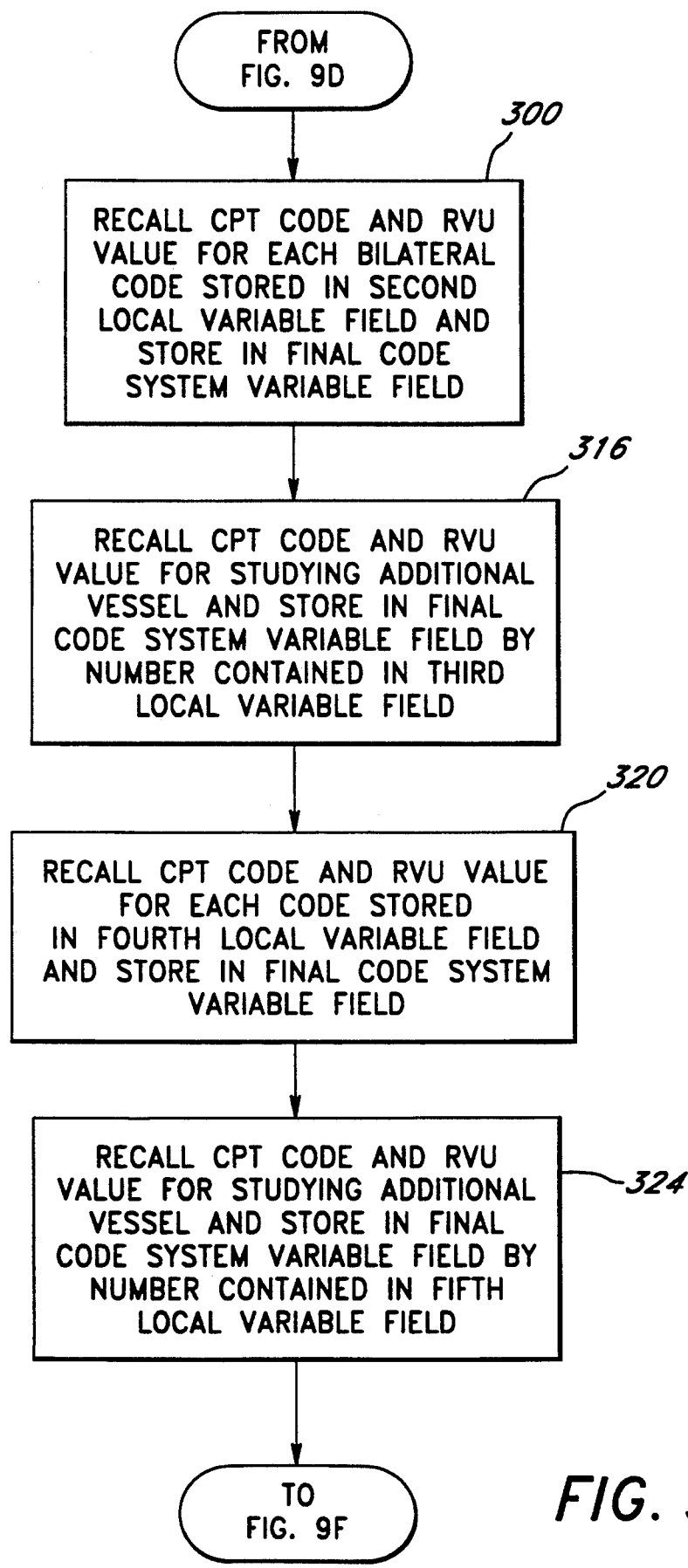

Returning to the decision block 308 illustrated in FIG. 9D, if the interactive program finds no additional special location modifiers in the raw codes stored in the first local variable, the interactive program advances straight to the activity block 300 (FIG. 9E).

Referring to FIG. 9E, at activity block 300, the interactive program recalls from memory the CPT codes and the RVU values for each bilateral code stored in the second local variable. After recalling the CPT codes and RVU values, the interactive program stores them in the final code system variable in the format described above (i.e., the RVU value followed by the associated CPT code).

The interactive program then advances to the next activity block 316 and recalls the CPT code and RVU value for studying an additional vessel in a particular vascular family. The interactive program stores the recalled CPT code and RVU value in the final code system variable by the number stored in the third local variable for each particular vascular family. The CPT codes and RVU values are stored in the format described above.

After storing to the final code system variable, the interactive program proceeds to the next activity block 320 and recalls the CPT codes and RVU values from memory for each code stored in the fourth local variable. The interactive program stored the recalled CPT codes and the RVU values in the final code system variable in the format described above. The interactive program then advances to the next activity block 324 and recalls the CPT codes and RVU values from memory for studying additional vessels in each vascular family. The interactive program stores the recalled CPT codes and RVU values in the final code system variable by the number stored in the fifth local variable for each particular vascular family. The CPT codes and RVU values are stored in the format described above.

Figure 9F:
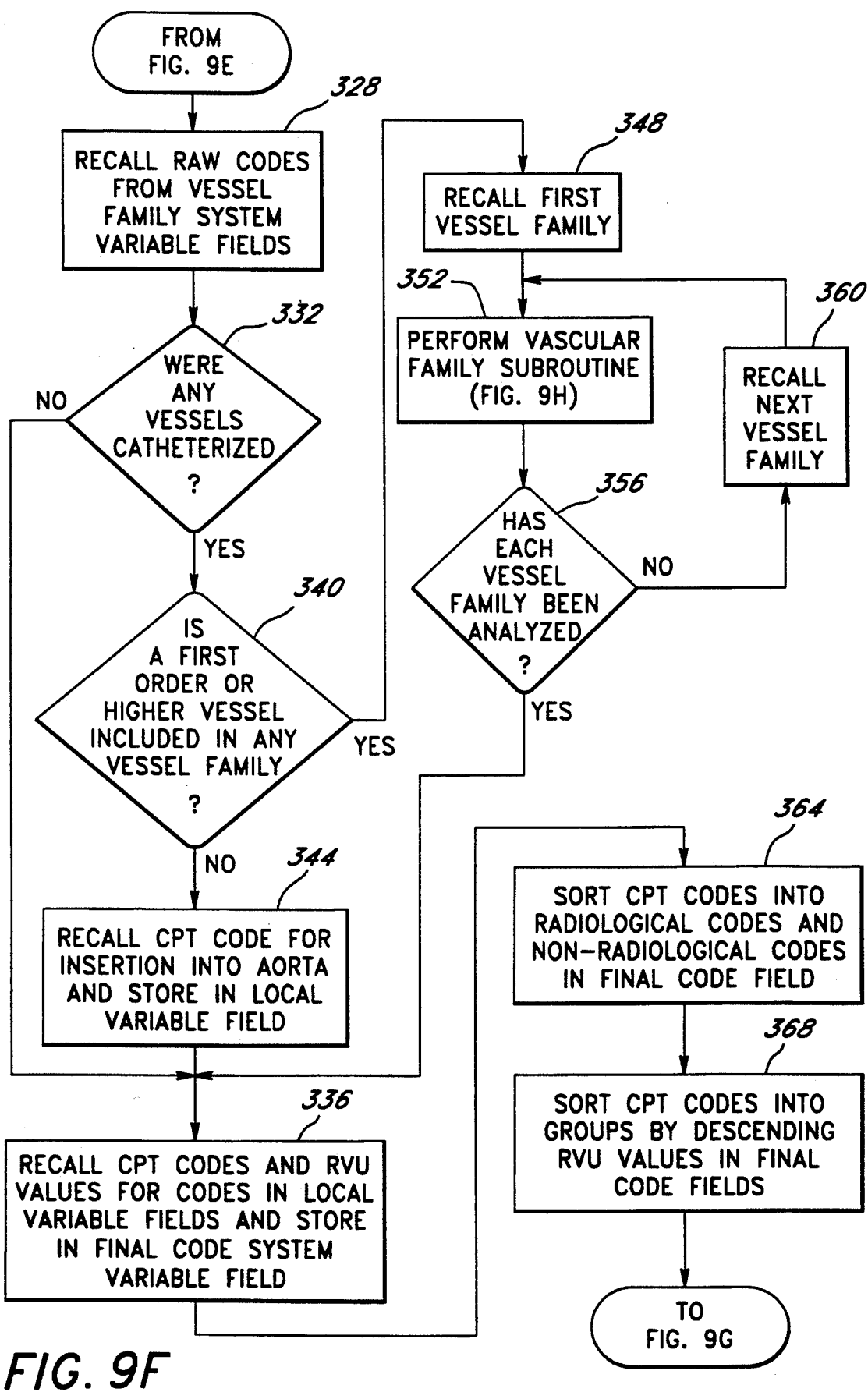

Referring to FIG. 9F, the interactive program advances to the next activity block 328 and stores the raw codes from the vascular family system variables in a sixth local variable. The interactive program then proceeds to a decision block 332 to determine if the selected procedures involve catheterization of any vessels. If no vessels were catheterized, the interactive program proceeds to an activity block 336.

If, however, vessels were catheterized in the selected procedures, the interactive program proceeds to determine the CPT codes and RVU codes for the raw codes contained in the vascular family system variables. Specifically, the interactive program proceeds to a decision block 340 to determine if any of the vascular family variables contain a first order or higher vessel. As mentioned above, the CPT coding system requires the interventionalist to identify the number of vascular families catheterized as well as the "order" of the vessel that the radiologist studied. Compensation depends, in part, upon the order of the vessel studied.

Figure 10:
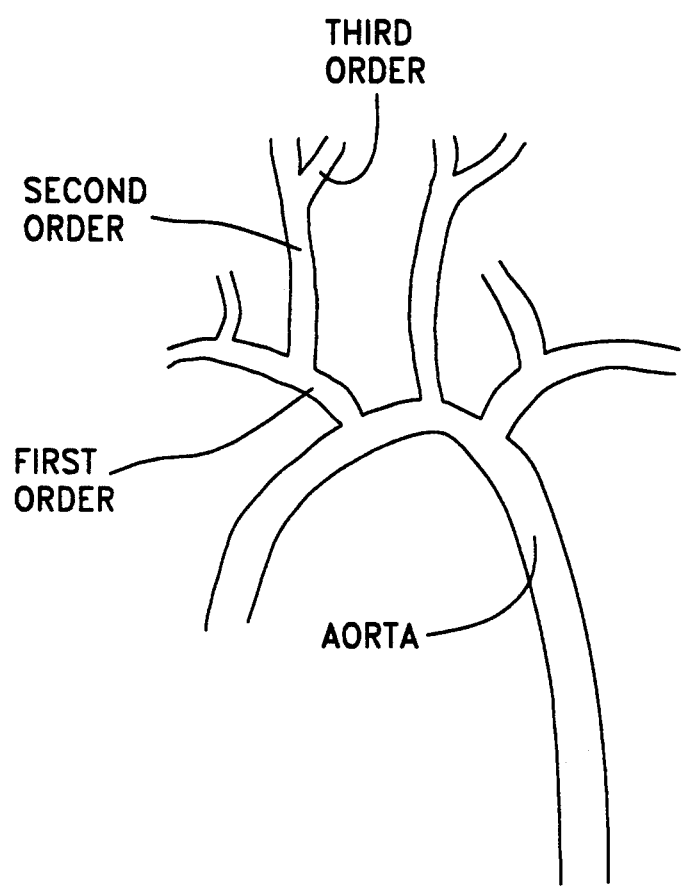
FIG. 10 is a schematic illustration of a plurality of vascular families branching from the aorta and indicating the order of vessels shown.

FIG. 10 illustrates several vascular families branching off of the aorta. As defined by the CPT coding system, a vessel family is a group of vessels that share a common vessel or origin arising from either the aorta or one of the vena cavae. The order of a vessel is defined as follows: a first order arterial branch is the first branch of a family that arises form the aorta; a second order vessel is the next branch or tributary of a first order vessel; and a third order vessel is the next branch or tributary of a second order vessel. FIG. 10 indicates the order of several vessels shown.

Referring back to FIG. 9F, if no vascular family contains a first or higher order vessel, the interactive system variable program precedes to an activity block 344 and determines the CPT code and RVU value for a non-selective catheterization (i.e., catheterization of the aorta or one of the vena cavae). That is, if the vascular family variables contain an indication that a vascular injection was performed but no first or higher order vessels were catheterized, the interactive program will account for a basic catheterization of either the aorta or the vena cava. The interactive program then stores the CPT code and RVU value to seventh local variable 220 (FIG. 1).

Returning to the decision block 340, if the selected procedures did involve catheterization of a first or higher order vessel, the interactive program proceeds to an activity block 348 were the interactive program recalls a first vascular family for the vascular family system variables. Then, at an activity block 352, the interactive program calls up a vascular family subroutine—which is discussed in detail below and illustrated in FIG. 9H through 9J—to determine the codes associated with the catheterization of any vessel of the first vascular family. After performing the vascular family subroutine, the interactive program proceeds to a decision block 356 and determines if each vascular family system variable has been analyzed by the vascular family subroutine. If all vascular family system variables have been analyzed, the interactive program advances to the activity block 336. If not, the interactive program proceeds to an activity block 360 and recalls the next vascular family system variable. This cycle continues until the interactive program has analyzed all vascular family system variables.

After analyzing each vascular family system field, the interactive program proceeds to the activity block 336 and recalls the CPT codes and RVU values for the codes stored in the corresponding local variables 220 (FIG. 1). The interactive program then stores the recalled CPT codes and RVU values in the final code system variable in the format specified above.

After storing all CPT codes associated with the selected procedures in the final code system variable, the interactive program advances to an activity block 364 and groups the codes in the final code system variable into radiological codes (e.g., 70,000 codes) and non-radiological codes (e.g., 30,000 and 90,000 codes). The interactive program then proceeds to the next activity block 368 and sorts each grouping in the final code system variable by descending RVU values. This step assures that the physician receives maximum payment for the performed procedures because Medicare and other insurance carriers compensates 100% of the fees for the first surgical CPT code listed, 50% of the fees for the next surgical CPT code listed and 25% of the fees for each following surgical CPT code. Thus, it is economically advantageous to list the CPT code having the largest RVU value first.

The interactive program preferably also has the capability of keeping track of the ICD-9 diagnostic codes most likely associated with the procedures selected by the user. Specifically, after sorting the final code system variable, the interactive program proceeds to an activity block 372 and recalls from memory all of the likely ICD-9 codes associated with the procedures that the user has selected. The ICD-9 codes are diagnostic codes specified by the International Classification of Diseases (9th revision). The interactive program stores these codes to a ICD-9 system variable.

After generating and ordering the CPT codes associated with the selected procedure, the interactive program takes the user back to the Main Menu (FIG. 3A). Referring back to FIG. 9G, the interactive program then proceeds to decision block 376 to determine if the user wants to select additional procedures. If the user does want to select additional procedures, the interactive program returns to the activity block 232 (FIG. 9B). If the user does not want to select additional procedures, the interactive program proceeds to a decision block 380 to determine if the user wants to delete any previously selected procedure. The user deletes procedures by clicking on a previously selected procedure button on an examination screen, and the interactive program proceeds to an activity block 384 to delete the associated raw codes from the raw code system variable. If the user returns to the Main Menu, the interactive program returns to the activity block 272 (FIG. 9C) to regenerate the CPT codes for the selected procedures by running through the final common pathway described above without the deleted codes.

Figure 9G:
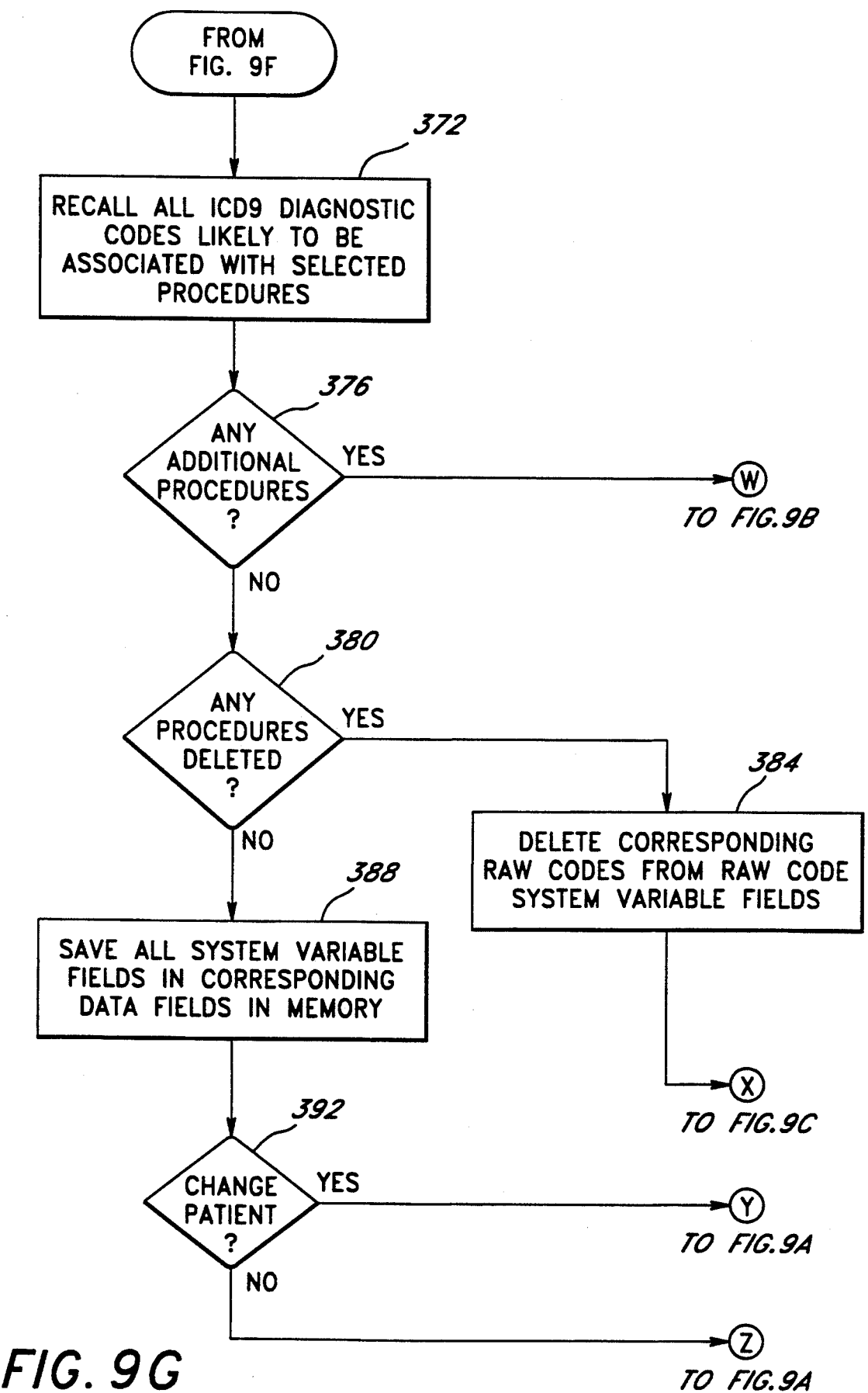

Returning to the decision block 380 illustrated in FIG. 9G, if the user does not delete procedures, the interactive program advances to an activity block 388 when the user clicks on the SAVE hotword 168. The interactive program then stores the system variables 214 to corresponding data fields in the nonvolatile memory 219.

Advantageously, the interactive program stores all the information required to recall each examination screen of a particular record. Thus, when the user recall a previous examination record, the interactive program constructs the examination screen as previously displayed, with each selected procedure button colored, with the procedure drawing highlighted according to the selected procedures and the corresponding textual description of the selected procedures displayed in the procedure screen field (FIG. 3D). The interactive program is able to reproduce each examination screen in this manner by storing the specifics of each system variable to a corresponding data field in the examination record stored on the hard disk.

After saving the examination record to the hard disk, the interactive program requests that the user indicate whether the user wants to view or create an examination record for another patient. Specifically, the interactive program proceeds to a decision block 392 and inquires whether the user wants to change patients. If the user wants to view or create an examination record of another patient, the interactive program returns to the initial decision block 204 (FIG. 9A). If the user wants to view or create another examination record for the same patient, the interactive program returns to the decision block 216 (FIG. 9A). The user also has the option to exit the interactive program at this stage or at any other stage of the interactive program by clicking on the QUIT hotword in the screen top field 150 (FIG. 3A).

Figure 9H:
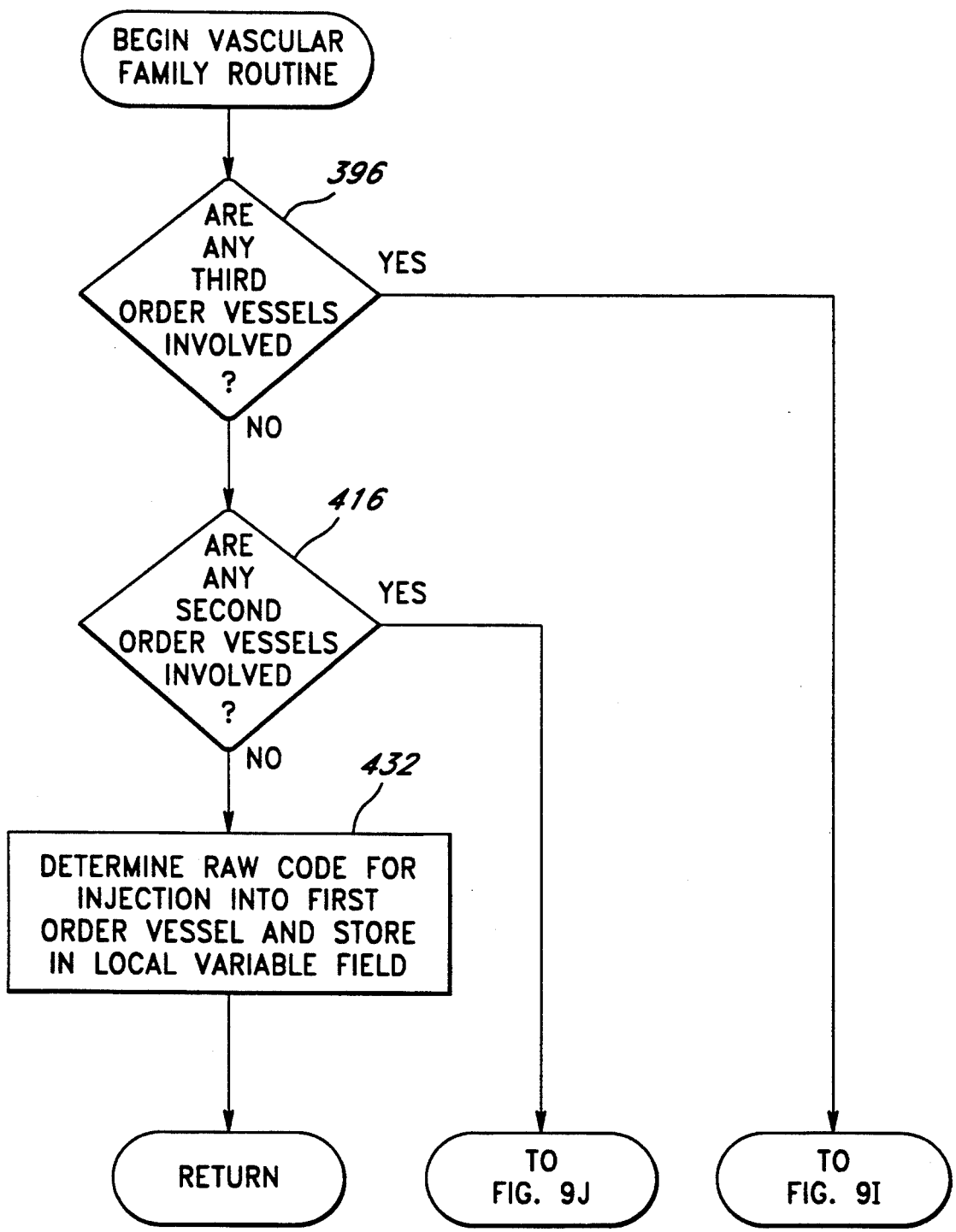
Figure 9I:
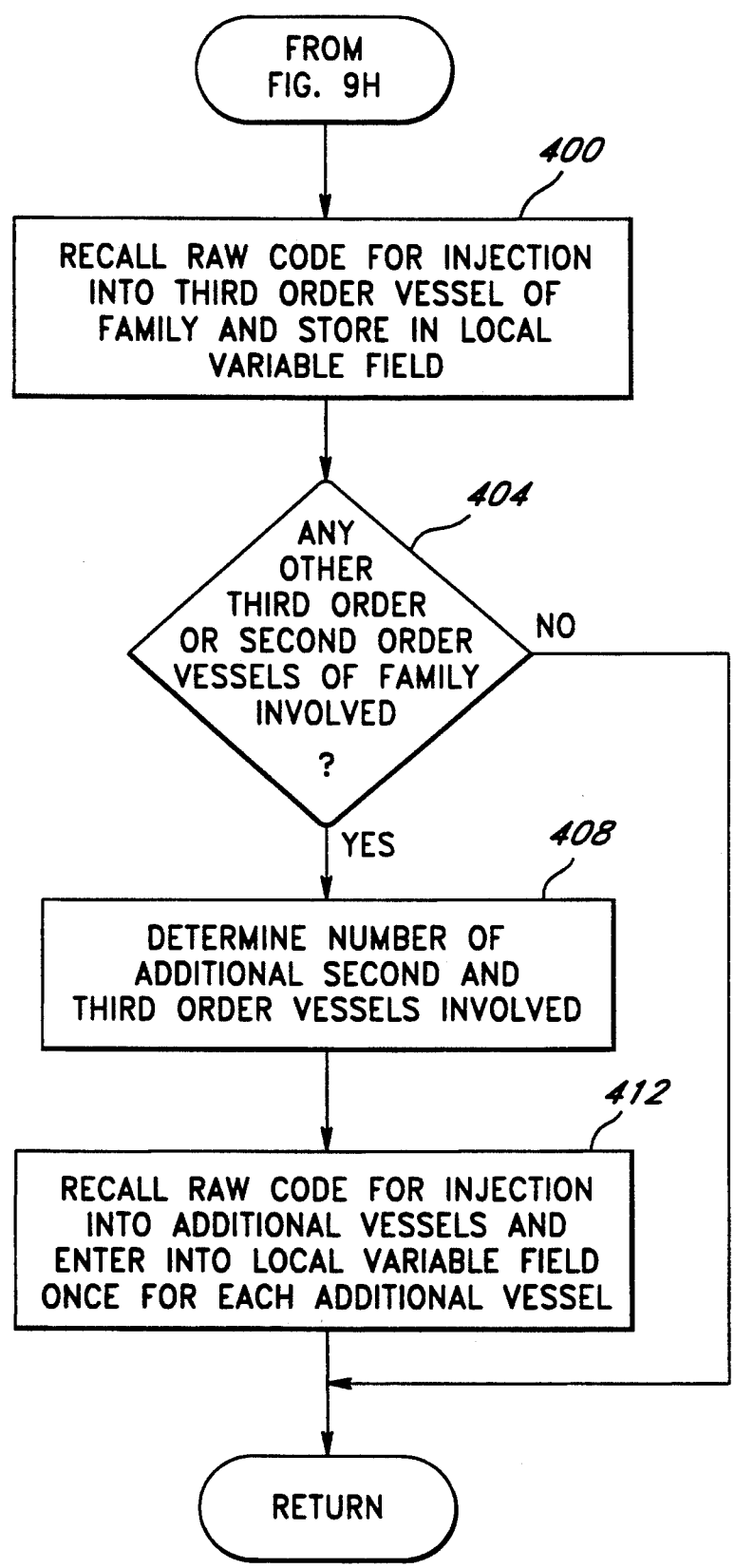
Figure 9J:
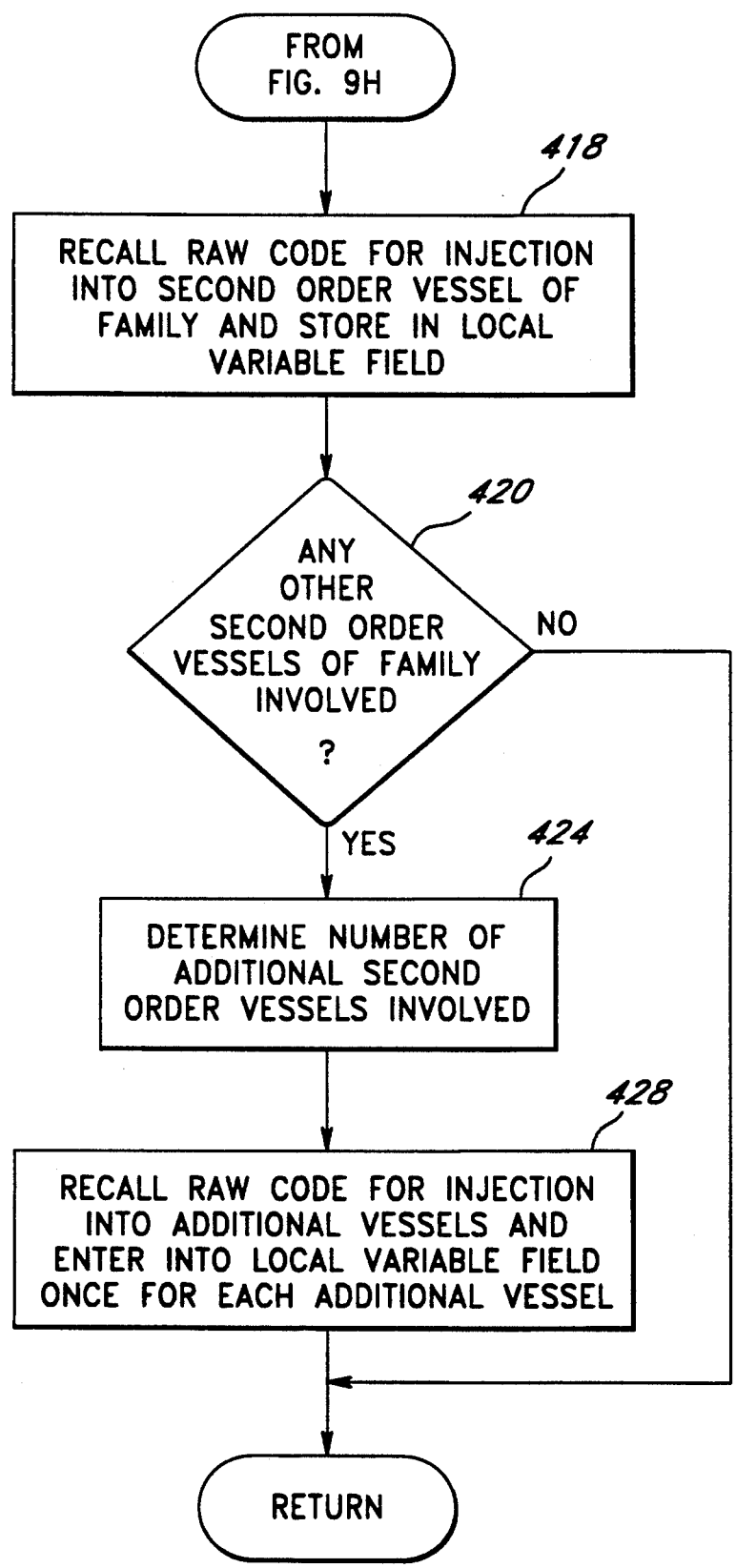

As indicated above, the interactive program analyzes the raw codes in the vascular family system variable code fields by performing the Vascular Family subroutine diagramed in FIG. 9H through 9J. The interactive program proceeds from the decision block 352 (FIG. 9F) to the start of the Vascular Family subroutine indicated by the start subroutine block on FIG. 9H. The interactive program then advances to a decision block 396 and determines whether any selected procedure involved the catheterization of any third order vessels of the vascular family being analyzed.

The interactive program determines if any third order vessels are involved by reviewing the code stored in the particular vascular family system variable. Each vascular family is represent by a three digit code with the least significant digit representing first order vessels in the vascular family, the middle digit representing second order vessels in the vascular family, and the most significant digit representing third order vessels in the vascular family. For every vessel in a particular vascular family catheterized during the selected procedures, the interactive program increments the digit corresponding to the catheterized vessels by one. For instance, if a set of selected procedures involved the catheterization of two third order vessels, four second order vessels and three first order vessels in a particular vascular family, the interactive program would represent the catheterization of the vascular family as 243.

The interactive program preferably stores several vascular family raw codes in a single system variable and recalls the vascular family subroutine for each system variable. The interactive program then runs through the subroutine for each vascular family code contained in the system variable. Specifically, the interactive program recalls a first vascular family code (i.e., the three digit code) from the system variable and runs through the vascular family subroutine. Then, the interactive program recalls the next vascular family code and again runs through the subroutine. The interactive program performs this routine until all vascular families in each vascular family system variable have been analyzed. In this manner, the interactive program calls up the subroutine fewer times to complete its analysis all of the vascular families, which speeds up the analysis.

Returning to decision block 396, the interactive program looks at the most significant digit to determine whether any third order vessels in a particular family were catheterized during the selected procedures. If the selected procedures involve catheterization of third order vessels, the interactive program proceeds to an activity block 400 illustrated in FIG. 9I and recalls the code and RVU value for injection into a third order vessel of the particular vascular family. The interactive program then stores the recalled code and RVU value in a local variable 220 (FIG. 1).

After storing the code and RVU value, the interactive program advances to a decision block 404 to determine whether any other second or third order vessels were catheterized during the selected procedures. Specifically, the interactive program decreases the numerical value of the most significant digit by one and adds the remainder to the numerical value contained at the middle digit. For example, the number of additional vessels in the above example would be five ((2−1)+4). If the selected procedure involved no additional vessels (i.e., the value calculated equals 0) then the interactive program returns back to activity block 352 (FIG. 9F).

If, however, the selected procedures involve catheterization of additional second or third order vessels, the interactive program advances to an activity block 408 and determines the number of additional second and third order vessels according to the above description. The interactive program then proceeds to an activity block 412 to recall the code and RVU value for injection into additional second and third order vessels for the particular vascular family. The interactive program stores this code and RVU value in a local variable 220 (FIG. 1) once for each additional vessel involved. The interactive program then returns to the activity block 352 (FIG. 9F).

Returning to the decision block 396 on FIG. 9H, if the selected procedures do not involve catheterization of any third order vessels, the interactive program proceeds to a following decision block 416 and determines whether the selected procedures involve catheterization of any second order vessels. If any of the selected procedures catheterized second order vessels, the interactive program proceeds to an activity block 418, illustrated in FIG. 9J, and recalls the code and RVU value for injection into a second order vessel of the particular family. The interactive program then stores the recalled code and RVU value in a local variable 220 (FIG. 1).

After storing the code, the interactive program advances to a decision block 420 to determine whether any other second order vessels were catheterized during the selected procedures. If the selected procedure involved no additional second order vessels, then the interactive program returns back to activity block 352 (FIG. 9F).

If, however, the selected procedures involve catheterization of additional second order vessels, the interactive program advances to an activity block 424 and determines the number of additional second order vessels. The interactive program then proceeds to an activity block 428 to recall the code and RVU value for injection into additional second order vessels for the particular vascular family. The interactive program stores this code and RVU value in a local variable once for each additional vessel involved. The interactive program then returns back to activity block 352 (FIG. 9F).

Returning to the decision block 416 in FIG. 9H, if the selected procedures did not catheterize any second order vessels, the interactive program proceeds to an activity block 432 and determines the code for catheterization of a first order vessel of the particular vascular family. The interactive program then stores the recalled code and RVU value to a local variable 214 (FIG. 1). After storing the recalled code and RVU value, the interactive program returns to the final common pathway at activity block 352 (FIG. 9F).

The final common pathway described above allows the interactive program to generate the CPT codes and RVU values associated with the selected medical procedures. The final common pathway accounts for interaction between many CPT codes without modifying each raw code associated with each procedure. Consequently, the final common pathway of the interactive program keeps track of associated codes as the user constantly changes selected procedures. Additionally, the interactive program is able to reproduce the exact examination screen by storing all information required to reproduce the screen with the particular patient examination record.

The foregoing invention has been described with respect to the generation of payment codes for radiological procedures. It should be understood that the invention could be used for the generation of similar codes for other medical procedures wherein one procedure may require multiple subprocedures having codes which should be included in billings and which must be analyzed to eliminate redundant codes.

Although this invention has been described in terms of a certain preferred embodiment, other embodiments apparent to those skilled in the art are also within the scope of this invention. Accordingly, the scope of the invention is intended to be defined only by the claims which follow.

What is claimed is:

1. A method of generating official billing codes in response to selected medical procedures, said method for use with a host computer of the type having a processing unit, memory, a monitor, and a user interface, said method comprising the steps of:
   providing a category of medical procedures;
   providing a collection of raw codes, each raw code corresponding to a medical procedure of said category of medical procedures;
   selecting a set of medical procedures from said category of medical procedures;
   generating a set of raw codes associated with the set of selected medical procedures by recalling specific raw codes from said collection which correspond to said set of selected medical procedures;
   analyzing said set of raw codes to compute a set of intermediate codes, said intermediate codes representing the interrelation of the set of selected medical procedures; and
   generating a set of said official billing codes from said set of intermediate codes by providing a collection of official billing codes corresponding to a collection of intermediate codes, and recalling specific official billing codes associated with said set of intermediate codes.

2. The method of claim 1 additionally comprising the step of storing said raw codes in a memory location of the processing unit.

3. The method of claim 1 additionally comprising the step of storing said intermediate codes in a memory location of the processing unit.

4. The method of claim 1, wherein said step of analyzing said set of raw codes comprises the steps of:
   comparing each raw code against the other raw codes in said set of raw codes associated with the set of selected medical procedures to determine whether said set of raw codes contains any raw code associated with any selected medical procedure of the set that is a subprocedure of another selected medical procedure of the set, and eliminating said raw code associated with the medical subprocedure to compute said set of intermediate codes; and
   storing said intermediate codes in a memory location of the processing unit.

5. The method of claim 1, wherein said collection of raw codes comprises at least one raw code which specifies that the associated medical procedure involves catheterization of a vessel, said raw code further specifying a vascular family of and an order of said catheterized vessel, and wherein said step of analyzing said set of raw codes comprises the steps of:
   evaluating whether any of raw codes associated with the selected set of medical procedures designates that any medical procedure of the selected set involves catheterization of a vessel; and
   if any of the medical procedures associated with the set of raw codes involve catheterization of a vessel, performing the steps of:
      examining each raw code associated with said medical procedures which involve catheterization of a vessel to determine the order of vessels catheterized in each vascular family involved in the selected medical procedures; and
      if any of the selected set of medical procedures involves catheterization of a third order vessel, performing the steps of:
         providing a collection of intermediate codes representative of catheterization procedures of third order vessels for each vascular family;
         recalling an intermediate code representative of the catheterization procedure of a third order vessel for each vascular family involved in the selected set of medical procedures; and
         storing the intermediate code for each vascular family in a memory location of the processing unit.

6. The method of claim 5, wherein, if the selected set of medical procedures involve catheterization of more than one third order vessel of a vascular family, said step of analyzing said set of raw codes additionally comprises the steps of:
   providing an intermediate code associated with the catheterization of additional second or third order vessels for each vascular family;
   recalling an intermediate code representative of each catheterization procedure of additional second or third order vessels for each vascular family involved in the selected medical procedures; and
   storing the associated intermediate code in a memory location of the processing unit once for each additional second or third order vessel of each vascular family involved in the selected medical procedures.

7. The method of claim 1, wherein said collection of raw codes comprises at least one raw code which specifies that the associated medical procedure involves catheterization of a vessel, said raw code further specifying a vascular family of and an order of said catheterized vessel, and wherein said step of analyzing said set of raw codes comprises the steps of:
   evaluating whether any of the raw codes associated with the selected set of medical procedures designates that any medical procedure of the selected set involves catheterization of a vessel; and
   if any of the selected set of medical procedures involve catheterization of a vessel, performing the steps of:
      examining each raw code associated with said medical procedures which involve catheterization of a vessel to determine the order of vessels catheterized in each vascular family involved in the selected medical procedures; and
      if any of the selected set of medical procedures involve catheterization of a second order vessel, performing the steps of:

providing a collection of intermediate codes representative of catheterization procedures of second order vessels for each vascular family;

recalling an intermediate code representative of the catheterization procedure of a second order vessel for each vascular family involved in the selected set of medical procedures; and storing the associated intermediate code for each vascular family in a memory location of the processing unit.

8. The method of claim 7, wherein, if the selected set of medical procedures involve catheterization of more than one second order vessel of a vascular family, said step of analyzing said set of raw codes additionally comprises the steps of:

providing an intermediate code associated with the catheterization of additional second order vessels for each vascular family;

recalling an intermediate code representative of each catheterization procedures of additional second order vessels for each vascular family involved in the selected set of medical procedures; and storing the associated intermediate code in a memory location of the processing unit once for each additional second order vessel of each vascular family involved in the selected medical procedure.

9. The method of claim 1, wherein said collection of raw codes comprises at least one raw code with specifies that the associated medical procedure involves catheterization of a vessel, said raw code further specifying a vascular family of and an order of said catheterized vessel, and wherein said step of analyzing said raw codes comprises the steps of:

evaluating whether any of the raw codes associated with the selected set of medical procedures specifies that any medical procedure of said set involves catheterization of a first order vessel;

providing an intermediate code associated with the catheterization of a first order vessel for each vascular family; and if any of the selected medical procedures involve catheterization of a first order vessel, performing the steps of:

recalling an intermediate code representative of the catheterization procedure of a first order vessel for each vascular family involved in the selected set of medical procedures; and storing the associated intermediate code for each vascular family in a memory location of the processing unit.

10. The method of claim 1, wherein said collection of raw codes comprises at least one raw code which specifies that the associated medical procedure involves a preselected anatomic location, and said method of analyzing said set of raw codes comprises the steps of:

evaluating whether any of the raw codes associated with the selected set of medical procedures involve a preselected anatomic location;

providing a collection of intermediate codes associated with medical procedures involving each preselected anatomic locating;

recalling intermediate codes associated with the selected medical procedures of said set which involve any of the preselected anatomic locations; and storing the associated intermediate code in a memory location of the processing unit.

11. The method of claim 1 additionally comprising the step of storing said official billing codes in a memory location of the processing unit.

12. The method of claim 11, wherein said official billing codes correspond to Current Procedural Terminology (CPT) codes.

13. A method of generating official billing codes in response to selected medical procedures, said method for use with a host computer of the type having a processing unit with volatile memory, nonvolatile memory, a monitor, a user interface and a data selector, said method comprising the steps of:

selecting a subset of medical procedures from a specified set of medical procedures;

analyzing said subset of selected medical procedures to determine if any of the medical procedures of said subset is a subprocedure of another selected medical procedure of said subset, and eliminating said subprocedures from said subset of selected medical procedures; and generating a set of official billing codes for said subset of selected medical procedures by:

providing a collection of official billing codes corresponding to said specified set of medical procedures; and recalling specific official billing codes associated with said selected medical procedures of said subset.

14. The method of claim 13 additionally comprising the step of analyzing said subset of selected medical procedures to determine if said subset of selected medical procedures contains duplicative medical procedures and eliminating any duplicative medical procedures from said subset of selected medical procedures.

15. A method of organizing medical examinations, said method for use with a host computer of the type having a processing unit with volatile memory, nonvolatile memory, a monitor, a user interface and a data selector, said method comprising the steps of:

selecting a subset of medical procedures from a specified set of medical procedures stored in the nonvolatile memory;

storing said subset of selected medical procedures in a first system variable of said volatile memory;

assigning a status to said subset of selected medical procedures and storing said status in a second system variable, said status being assigned by selecting said status from a specified set of progressive stages associated with said specified set of medical procedures, said specified set of progressive stages being stored in the nonvolatile memory; and creating a recording having a plurality of data fields in a data base stored on the nonvolatile memory and writing said first and second system variables to corresponding data fields of said record.

16. The method of claim 15, wherein said status is selected from a group of progressive stages comprising planned, performed, reviewed and billed.

17. The method of claim 15, additionally comprising the step of:

providing a set of official billing codes for said set of selected medical procedures;

recalling a subset of specific official billing codes associated with said subset of selected medical procedures;

storing said subset of official billing codes in a system variable of said volatile memory; and writing said system variable to a corresponding data field of said record.

18. The method of claim 15, wherein said step of selecting a subset of selected medical procedures comprises the steps of:
   displaying on the monitor a plurality of examination screens which display said set of specific medical procedures; and
   using the user interface or data selector to select a subset of medical procedures from said set of medical procedures displayed on said examination screens which the user plans to perform or has performed.

19. The method of claim 18 additionally comprising the step of indicating the selected subset of medical procedures displayed on an examination screen by displaying a graphical representation on the monitor of an anatomic location involved in the selected medical procedure of said subset of medical procedures.

20. The method of claim 19 additionally comprising the steps of:
   storing said displayed graphical representation in a system variable specific to said examination screen display; and
   writing said system variable to a corresponding data field of a record on the nonvolatile memory such that when the user recalls said examination screen, said graphical representation is redisplayed on the monitor.

21. The method of claim 11, wherein said step of generating a set of billing codes additionally comprises the step of writing said official billing codes in the memory.

22. The method of claim 11, wherein said step of generating a set of billing codes additionally comprises spooling said official billing codes in the memory to the printer.

23. The method of claim 12, wherein said step of generating billing codes additionally comprises the steps of:
   providing a collection of relative value units associated with the CPT billing codes;
   recalling specific relative value units associated with said set of CPT billing codes stored in the memory location of the processing unit; and
   sorting said relative value units in descending order.

* * * * *

UNITED STATES PATENT AND TRADEMARK OFFICE
CERTIFICATE OF CORRECTION

PATENT NO. : 5,325,293
DATED : June 28, 1994
INVENTOR(S) : Howard L. Dome

It is certified that error appears in the above-indentified patent and that said Letters Patent is hereby corrected as shown below:

```
Column 1, line 11, change "particulate" to --particular
Column 1, line 32, change "procedure" to --procedural--
Column 1, line 35, change "rubric," to --rubric.--

Column 22, line 53, change "recording" to --record--
```

Signed and Sealed this

Twenty-first Day of November, 1995

Attest:

BRUCE LEHMAN

Attesting Officer  Commissioner of Patents and Trademarks